US007637980B2

(12) United States Patent
Smith et al.

(10) Patent No.: US 7,637,980 B2
(45) **Date of Patent: *Dec. 29, 2009**

(54) METHOD OF INCREASING PHOTOSYNTHESIS IN PLANTS COMPRISING AN EXPOSURE THEREOF TO LIPOCHITOOLIGOSACCHARIDES AND COMPOSITIONS THEREFOR

(75) Inventors: Donald L. Smith, Ste-Anne de Bellevue (CA); Balakrishnan Prithiviraj, Ste-Anne de Bellevue (CA); Xiaomin Zhou, Ste-Anne de Bellevue (CA); Alfred Souleimanov, Montreal (CA)

(73) Assignee: McGill University, Montreal (CA)

( * ) Notice: Subject to any disclaimer, the term of this patent is extended or adjusted under 35 U.S.C. 154(b) by 166 days.

This patent is subject to a terminal disclaimer.

(21) Appl. No.: 11/779,736

(22) Filed: Jul. 18, 2007

(65) Prior Publication Data

US 2008/0015109 A1 Jan. 17, 2008

Related U.S. Application Data

(63) Continuation of application No. 10/110,293, filed as application No. PCT/CA00/01192 on Oct. 6, 2000, now Pat. No. 7,250,068.

(30) Foreign Application Priority Data

Oct. 8, 1999 (CA) .................................... 2285727

(51) Int. Cl.
*C05F 11/08* (2006.01)
*C08B 37/08* (2006.01)

(52) U.S. Cl. ............................... 71/11; 514/25; 514/61; 536/20

(58) Field of Classification Search ....................... None
See application file for complete search history.

(56) References Cited

U.S. PATENT DOCUMENTS 4,169,716 A 10/1979 Ashmead ........................ 71/77
5,175,149 A 12/1992 Stacey et al. .................. 514/23

FOREIGN PATENT DOCUMENTS

AT 406 324 4/2000
DE 196 33 502 12/1998
WO WO 00/04778 2/2000

OTHER PUBLICATIONS

John, M. et al "Cell signalling by oligosaccharides" Trends in Plant Science (1997) vol. 2, No. 3, pp. 111-115.*
Schlaman, H. et al "Chitin oligosaccharides can induce cortical cell division in root cells . . . " Development 124 (1997) pp. 4887-4895.*
Translation of DE 19633502 (1998).*
Cocking et al. "Interaction of rhizobia with non-legume crops for symbiotic nitrogen fixation nodulation." *NATO ASI Series, Series G.:Ecologica Sciences*, vol. G37, pp. 197-205 (1995.).
Horst et al. "Growth of tobacco protoplasts stimulated by synthetic lipo-chitooligosaccharides" *Science*, vol. 269, No. 5225, pp. 841-843 (1995.).
Hani et al. "Potential of rhibozium and bradyrhizobium species as plant growth promoting rhizobacteria on on-legumes". *Plant & Soil*, vol. 204, No. 1, pp. 57-67 (1998). abstract only.
Imsande. "Enhanced nitrogen fixation increases net photosynthetic output and seed yield of hydroponically grown soybean". *Journal of Experimental Botany*, vol. 39, No. 206, pp. 1313-1322 (1988). abstract only.
Stuart et al. "Applied aspects of the gibberellins" *Ann. Rev. Plant Physiol.* vol. 12, pp. 369-394 (1961).
Ovtsyna et al. "Comparison of characteristics of the nodX genes . . . " *MPMI* vol. 12, No. 3. pp. 252-258 (1999).
Derwent abstract of DE 19633502 (1998).

* cited by examiner

*Primary Examiner*—Leigh C Maier
(74) *Attorney, Agent, or Firm*—Merchant & Gouls P.C.

(57) ABSTRACT

The present invention relates to agriculture. More particularly, the invention relates to a method of increasing photosynthesis of a plant and more particularly of crop plants. In addition, the invention relates to a method of increasing photosynthesis and/or yield in crop plants, comprising an exposure thereof to lipo-chitooligosaccharides, and compositions therefor. Further, the invention relates to an agricultural composition for enhancing a plant crop photosynthetic rate and/or growth thereof comprising a photosynthetic rate-promoting amount of at least one lipo chitooligosaccharide (LCO) together with an agriculturally suitable carrier and methods using same.

3 Claims, 9 Drawing Sheets

Photosynthesis
(µmol CO2 m-2s-1)
25
20
15
10
5
0
a
b
b
a
Control
LCO 10-6
LCO 10-8
LCO 10-10

Stomatal conductance
(mol H2O m-2 s-1)
0,14
0,12
0,10
0,08
0,06
0,04
0,02
0,00
a
a
a
a
Control
LCO 10-6
LCO 10-8
LCO 10-10

Intercellular CO2
(µmol mol air-1)
200
150
100
50
0
a
b
b
b
Control
LCO 10-6
LCO 10-8
LCO 10-10

Transpiration
(mmol H2O m-2s-1)
3
2
1
0
a
b
b
a
Control
LCO 10-6
LCO 10-8
LCO 10-10

Phtosynthesis rate (umol CO2 m-2s-1)
16 14 12 10 8 6 4 2 0
b ab ab a
control 10-6 10-8 10-10
LCO concentrations Stomata conductance (mol H2O m-2 s-1)
0,35 0,30 0,25 0,20 0,15 0,10 0,05 0,00
b ab ab a
control 10-6 10-8 10-10
LCO concentrations Intercellular CO2 concentration (umol CO2 mol-1)
300 250 200 150 100 50 0
a a a a
control 10-6 10-8 10-10
LCO concentrations Transpiration rate (mmol H2O m-2s-1)
7 6 5 4 3 2 1 0
b ab ab a
control 10-6 10-8 10-10
LCO concentrations Photosynthesis (μmol CO2 m-2s-1)
0
2
4
6
8
10
12
14
16
Control
LCO 10-8
LCO 10-10
a
b
a Stomatal conductance (mol H2O m-2s-1)
0,00
0,05
0,10
0,15
0,20
0,25
Control
LCO 10-8
LCO 10-10
a
b
a Ci (μmol CO2/mol air)
0
50
100
150
200
250
300
Control
LCO 10-8
LCO 10-10
a
a
a Transpiration (mmolH2Om-2s-1)
0
1
2
3
Control
LCO 10-8
LCO 10-10
a
b
a

METHOD OF INCREASING PHOTOSYNTHESIS IN PLANTS COMPRISING AN EXPOSURE THEREOF TO LIPOCHITOOLIGOSACCHARIDES AND COMPOSITIONS THEREFOR

This application is a Continuation of application Ser. No. 10/110,293 filed Nov. 13, 2002, and which application(s) are herein incorporated by reference.

FIELD OF THE INVENTION

The present invention relates to agriculture. More particularly, the invention relates to a method of increasing photosynthesis of a plant and more particularly of a crop plant. In addition, the invention relates to a method of increasing photosynthesis and/or growth and/or yield in crop plants, comprising an exposure thereof to lipo-chitooligosaccharides, and compositions therefor.

BACKGROUND OF THE INVENTION

Bacteria of the genera *Rhizobium, Bradyrhizobium, Sinorhizobium* and *Azorhizobium*, collectively known as the rhizobia, form specialized organs called nodules on the roots, and sometimes stems, of legumes and fix atmospheric nitrogen within these structures. Nodule formation is a highly specialized process that is modulated by signal molecules. In general, this phase of the interaction is a two step process. Initially, plant-to-bacteria signal molecules, usually specific flavonoids or isoflavonoids, are released by roots of the host plants. In response to the plant-to-bacteria signals the microsymbiont releases bacteria-to-plant signal molecules, which are lipo-chitooligosaccharides (LCOs), so called nod factors (also nol and noe) genes very rapidly (only a few minutes after exposure) and at very low concentrations ($10^{-7}$ to $10^{-8}$ M) (Peters et al., 1986). Generally this is through an interaction with nodD, which activates the common nod genes, although the situation may be more complex, as is the case in *B. japonicum*, where nod$D_1$, nod$D_2$ and nodVW are involved (Gillette & Elkan 1996; Stacey 1995). Nod genes have been identified in the rhizobia that form nitrogen fixing relationships with numbers of the Fabiaceae family (see U.S. Pat. No. 5,549,718 and references therein). Recently, the plant-to-bacteria signal molecules have been shown to promote soybean nodulation and nitrogen fixation under cool soil temperatures (CA U.S. Pat. No. 2,179,879) and increase the final soybean grain yield on average of 10% in the field and up to 40% under certain conditions. (Long, 1989; Kondorosi, 1991; Schenes et al., 1990; Boone et al, 1999). Among the products of the nod genes induced by the plant phenolic signal molecules are various enzymes involved in the synthesis of a series of lipo chitooligosaccharides (LCOs) (Spaink, 1995; Stacey, 1995). These newly synthesized LCOs act as bacterium-to-plant signals, inducing expression of many of the early nodulin genes (Long, 1989).

LCO signal molecules are composed of three to five 1-4 β linked acetylglucosamine residues with the N-acetyl group of the terminal non-reducing sugar replaced by an acyl chain. However, various modifications of the basic structure are possible and these, at least in part, determine the host specificity of rhizobia (Spaink et al., 1991; Schultze et al., 1992).

Lipo-chitiooligosaccharides are known to affect a number of host plant physiological processes. For example, they induce: root hair deformation (Spaink et al., 1991), ontogenyof compete nodule structures (Fisher and Long, 1992; Denarie and Cullimore, 1993), cortical cell division (Sanjuan et al., 1992; Schlaman et al., 1997) and the expression of host nodulin genes essential for infection thread formation (Horvath et al., 1993; Pichon et al., 1993, Minami et al., 1996). LCOs have also been shown to activate defense-related enzymes (Inui et al., 1997). These bacterium-to-plant signals exert a powerful influence over the plant genome and, when added in the absence of the bacteria, can induce the formation of root nodules (Truchet et al., 1991). Thus, the bacteria-to-plant signals can, without the bacteria, induce all the gene activity for nodule organogenesis (Denarie et al., 1996; Heidstra & Bisseling, 1996). Moreover, the above-mentioned activities induced by LCOs can be produced by concentrations as low as $10^{-14}$ M (Stokkermans et al. 1995). The mutual exchange of signals between the bacteria and the plant are essential for the symbiotic interaction. Rhizobia mutants unable to synthesize LCOs will not form nodules. Analysis of the *B. japonicum* nod genes indicates that ability to induce soybean nodulation requires at least: 1) a basic tetrameric Nod factor requiring only nodABC genes or 2) a pentameric LCO (C18:1, C16:0 or C16: fatty acid and a methyl-fucose at the reducing end, sometimes acetylated) requiring nodABCZ genes (Stokkermans et al. 1995).

When added to the appropriate legume, LCOs can cause the induction of nodule meristems (Denarie et al., 1996), and therefore cell division activity. LCOs have also been shown to induce cell cycle activities in an in vitro system: (a carrot embryogenesis system) at levels as low as $10^{-14}$ M (De Jong et al. 1993).

A chemical structure of lipo chitooligosaccharides, also termed "symbiotic Nod signals" or "Nod factor", has been described in U.S. Pat. Nos. 5,549,718 and 5,175,149. These Nod factors have the properties of a lectin ligand or lipo-oligosaccharide substances which can be purified from bacteria or synthesized or produced by genetic engineering.

The process of $N_2$ fixation is energy intensive requiring about 10-20% of the carbon fixed by the plant. It has been estimated that an average of about 6 mg of carbon is required per mg of nitrogen fixed (Vance and Heichel, 1991). Enhanced photosynthesis, due to the *Bradyrhizobium*-soybean association has been previously reported. Imsande (1989a,b) reported enhanced net photosynthesis and grain yield in soybean inoculated with *Bradyrhizobium japonicum* compared with plants that were not inoculated but adequately supplemented with N fertilizer. Recently, Phillips et al., (1999) showed that lumichrome might act as a signal molecule in the rhizosphere of alfalfa plants, leading to increased respiration and net carbon assimilation during early stages of the *Sinorhizobium meliloti*-alfalfa symbiosis.

Methods to increase plant dry matter accumulation and yield are essential as world population is projected to increase by 4 billion (66%) during the next fifty years (United Nations, Population Division, 1998). In the last fifty years world crop output increased by 2.5 fold, with little increase the area of land cropped (Hoisington et al., 1999). Given the projected increase in world population we must provide another 2.5 fold increase during the next 50 years if everyone is to have reasonably reliable access to food (James, 1997). However, the primary causes of increased food production during the last 50 years (increases in harvest index, the amount of land under irrigation and the use of fertilizers, particularly N fertilizer) are largely exhausted. A century of plant breeding has resulted in little or no increase in the photosynthetic rates of most crop plants (Moss and Musgrave, 1971; Evans 1975, 1980). There thus remains a tremendous need to increase the photosynthetic rates and growth of crop plants. There also remains a need to increase production of crop plants.

There have been considerable efforts to enhance photosynthesis in crop plants with a view to increase plant productivity. Makela et al., (1999) reported enhanced photosynthesis under drought and salinity stress in tomato and turnip rape following foliar application of glycinebetanine at very low concentrations. Foliar application of methanol also increased photosynthesis in a number of plants (Noumora and Benson, 1991). Johnson and Stelizer (1991) reported increased photosynthesis in loblolly pine by application of sub-lethal doses hexazinone.

While the effects of plant-to-bacteria signal molecules (i.e. isoflavones) on nodulation, nitrogen fixation, growth and protein yield of legumes, such as soybean, and on bacteria-to-plant signal molecules (LCOs) on nodulation and nitrogen fixation in legumes have been described under certain conditions, the effect of the bacteria-to-plant signal molecules on the growth of non-legumes is unknown. In fact, the role of such bacteria-to-plant signal molecules on non-legumes has yet to be reported. In addition, the effect of LCOs on processes other than nodulation of legumes has yet to be described. Moreover, while LCOs have been associated with a growth-promoting effect in the early stages of the initiation of the symbiotic relationship between plant and bacteria, it remains to be determined whether LCOs can have an effect on plants at later stages of their life cycle.

There thus remains a need to assess the effect of LCOs on plant growth and especially on later stages thereof. Moreover, there remains a need to assess whether LCO comprising compositions can have an effect on the synthetic rate and/or growth of plants in general and especially of non-legume plants.

There also remains a need to better understand the workings of the complex homeostatic system which is involved in the regulation of photosynthesis. Moreover, there remains a need to assess the role of LCOs on photosynthesis of plants.

The present invention seeks to meet these and other needs.

The present description refers to a number of documents, the contents of which are herein incorporated by reference in their entirety.

SUMMARY OF THE INVENTION

The invention concerns a composition for enhancing the photosynthetic rate, and/or growth, and/or yield of a plant and especially of a crop plant. More specifically, the present invention relates to a composition comprising an LCO which can increase the photosynthetic rate, and/or growth, and/or yield of a legume, in addition to acting as a trigger to initiate legume symbiotic nitrogen fixation. More particularly, the invention relates to methods and compositions to enhance the photosynthetic rate, and/or growth, and/or yield of a plant and especially of a crop plant grown under field conditions. In certain embodiments, the plant is a non-legume. In further embodiments, the invention relates to methods and compositions to increase the photosynthetic rate, and/or growth, and/or yield of a legume, more particularly soybean, and especially to a legume grown under field conditions.

Surprisingly, the compositions of the present invention act not only on a legume such as soybean, but on plants in general, as exemplified with a number of non-legume crops. More specifically, these non-legume crops are exemplified with diversified and evolutionary divergent crops such as corn, rice (Poaceae); melon (Cucurbitaceae); canola (Brassicaceae); apple (Rosaceae); and grape (Vitaceae). The present invention thus also refers to compositions for enhancing photosynthetic rate, and/or growth, and/or yield of non-legumes. More particularly, the invention relates to compositions comprising an LCO for enhancing photosynthetic rate, and/or growth, and/or yield of non-legumes. Non-limiting examples of such non-legumes include cotton, corn, rice, canola, potato, cucumber, cantaloupe, melon, lettuce, apple, grape and beet.

Broadly therefore, the present invention relates to compositions comprising an LCO for promoting growth of a crop. Non-limiting examples of plant crops include monocot, dicot, members of the grass family (containing the cereals), and legumes.

More specifically, therefore, the present invention concerns the demonstration that an administration of LCOs to a plant significantly increases the photosynthetic rate thereof. More particularly, the present invention demonstrates that spraying LCOs on the leaves of a plant (e.g. a foliar application) significantly increases the photosynthetic rate thereof. The present invention therefore relates to compositions to increase the photosynthetic rate of plants in general. In addition, the present invention relates to methods of increasing the photosynthetic rate of evolutionary divergent plants, comprising an application of an agriculturally effective dose of LCOs. In a particularly preferred embodiment, the invention relates to an acute application of LCOs by a spraying of the leaves of the plants and to its effect on the growth and/or yield of plants and especially of field grown plants.

In a particular set of experiments, a composition of the present invention, comprising an LCO, was shown to significantly enhance the photosynthetic rate of evolutionary divergent plants such as soybean (Fabaceae), corn, rice (Poaceae), melon (Cucurbitaceae), canola (Brassicaceae), apple (Rosaceae) and grape (Vitaceae), under greenhouse conditions.

In another set of experiments in the field, a composition of the present invention comprising an LCO was shown to significantly enhance the photosynthetic rate of soybean, corn, apple and grape.

While the present invention has been demonstrated using evolutionary divergent plants, the invention should not be so limited. Indeed, it will be clear to a person skilled in the art to which the present invention pertains, that based on the evolutionary distance between the types of plants tested and their similar response to an application of LCOs, that it is expected that other types of plants should respond similarly to the LCO application, by displaying an increase in the photosynthetic rate and/or yield thereof. Of note, the group of Smith et al. (the group from which the instant invention stems) has also shown that LCOs can significantly enhance seed germination and/or seedling emergence and/or growth, and/or break the dormancy of numerous types of non-legume plant families, including Poaceae, Cucurbitaceae, Malvaceae, Asteraceae, Chenopodiaceae and Solonaceae. More specifically, the non-legume crops used included corn, cotton, cantaloupe, lettuce, potato and beet. Thus, the biological activity of LCOs on early stages of plants in general has also been demonstrated.

Based on (1) the evolutionary divergence of the tested crops, which display an increased photosynthetic rate after LCO treatment; and (2) the effect of LCO on germination, and seedling emergence (and of the breaking of dormancy of potato tubers) of evolutionary divergent plants, it is expected that the photosynthetic rates and yield-increasing effects demonstrated by the methods and compositions of the present invention can be applied to plants in general. More particularly, it relates to compositions and methods for different plant families including but not limited to Poaceae, Cucurbitaceae, Malvaceae, Asteraceae, Chenopodiaceae, Brassicaceae, Rosaceae, Vitaceae, Fabaceae and Solonaceae. More specifically, crops within the scope of the present invention include without limitation corn, cotton, cantaloupe, melon, cucumber, canola, lettuce, potato, apple, grape and beet. Non-limiting examples of crop plants also include monocot, dicot, members of the grass family (containing the cereals), and legumes.

Thus, the present invention relates to agricultural compositions comprising at least one LCO (and methods of using same) for promoting photosynthetic rate increases and/or increase in yield of a crop. It should be clear to a person skilled in the art that other photosynthetic rate increasing-, and/or yield-increasing compounds could be added to the compositions of the present invention.

The Applicant is the first to show that a composition comprising an LCO can have a significant effect on the photosynthetic rate of legumes. Moreover, the Applicant is the first to show the surprising effect of signal molecules involved in the bacteria-legume signalling on the photosynthetic rate and growth of non-legume plants.

It should also be understood that conventional plants and genetically engineered plants can be used in accordance with the present invention. In one particular and preferred embodiment of the present invention, non genetically-engineered plants are treated with the composition and/or method of the present invention.

While the photosynthetic rate and/or yield enhancing capabilities of the compositions of the instant invention are demonstrated under field conditions with corn, apple, grape and soybean, it is expected that other crops should also show the same type of response to LCOs treatment. These plants include without limitation significantly divergent plants in ten distinct families: (1) corn, the only monocot tested herein, in the family of grasses (Poaceae), which also contains the cereals; (2) cucumber and cantaloupe, the later being a plant used horticulturally, and being slow to germinate at low temperature [its base temperature is about 14° C.] (Cucurbitaceae); (3) cotton, one of the most important fibre crops on the planet (Malvaceae); (4) lettuce (Asteraceae); (5) beet (Chenopodiaceae); (6) potato, a very important crop (Solonaceae, which also includes tobacco, peppers and tomato); and two families of legumes (7) canola, representing the mustard group (Brassicaceae) and (8) soybean (representative of oil seed crop), bean (representative of a crop for human consumption) and red clover and alfalfa (forage legumes) (all of the Fabaceae family); (9) apple, representing Rosaceae; and (10) grape, representing Vitaceae.

In view of the evolutionary distance between the above-listed plants, and of their similar response to LCO treatment under greenhouse conditions or field conditions, it can be predicted that such results will apply to crop plants in general. It follows that a person skilled in the art can adapt the teachings of the present invention to other crops. Non-limiting examples thereof include tobacco, tomato, wheat, barley, rice, sunflower and plants grown for flower production (daisy, carnation, pansy, gladiola, lilies and the like). It will be understood that the compositions can be adapted to specific crops, to meet particular needs.

In accordance with one embodiment of the present invention, there is thus provided an agricultural composition for enhancing a plant crop photosynthetic rate and/or growth thereof comprising a photosynthetic rate-promoting amount of at least one lipo-chitooligosaccharide (LCO) together with an agriculturally suitable carrier.

In accordance with another embodiment of the present invention, there is therefore provided a use of an agricultural composition for enhancing a plant crop photosynthetic rate and/or growth thereof comprising a photosynthetic rate-promoting amount of at least one lipo-chitooligosaccharide (LCO) together with an agriculturally suitable carrier.

In accordance with yet another embodiment of the present invention, there is provided a method for increasing the photosynthetic rate and/or growth of a plant, comprising a treatment of a leaf of a plant with a composition comprising an agriculturally effective amount of a lipo chitooligosaccharide (LCO) in admixture with an agriculturally suitable carrier medium, wherein the effective amount enhances the photosynthetic rate and/or growth of the plant in comparison to an untreated plant.

In addition, in accordance with another embodiment of the present invention, there is therefore provided a method for enhancing the photosynthetic rate and/or growth of a plant crop comprising incubating a rhizobial strain which expresses a lipo chitooligosaccharide (LCO) in the vicinity of a leaf of the plant such that the LCO enhances the photosynthetic rate and/or growth of the plant crop as compared to an untreated plant.

The terms "lipochitin oligosaccharide" and "lipo-chitooligosaccharide" are used herein interchangeably.

The terminology "grown under field conditions" will be understood to cover the conditions to which a plant is subjected when grown in the field, as opposed to when grown under more controlled conditions, such as greenhouse conditions.

As used herein, the term "LCO" refers broadly to a Nod factor which is under the control of at least one nodulation gene (nod gene), common to rhizobia. LCO therefore relates to a bacteria-to-plant signal molecule which induces the formation of nodules in legumes and enables the symbiotic bacteria to colonize same. Broadly, LCOs are lipo chitooligosaccharide signal molecules, acting as phytohormones, comprising an oligosaccharide moiety having a fatty acid condensed at one of its end. An example of an LCO is presented below as formula I in which:

G is a hexosamine which can be substituted, for example, by an acetyl group on the nitrogen, a sulfate group, an acetyl group and/or an ether group on an oxygen, $R_1$, $R_2$, $R_3$, $R_5$, $R_6$ and $R_7$, which may be identical or different, represent H, $CH_3CO$—, $C_xH_yCO$— where x is an integer between 0 and 17, and y is an integer between 1 and 35, or any other acyl group such as for example a carbamyl, $R_4$ represents a mono-, di- or triunsaturated aliphatic chain containing at least 12 carbon atoms, and n is an integer between 1 and 4.

More specific LCOs from *R. meliloti* have also been described in U.S. Pat. No. 5,549,718 as having the formula II in which R represents H or $CH_3CO$— and n is equal to 2 or 3.

Even more specific LCOs include NodRM, NodRM-1, NodRM-3. When acetylated (the R=$CH_3CO$—), they become AcNodRM-1, and AcNodRM-3, respectively (U.S. Pat. No. 5,545,718).

LCOs from *B. japonicum* have also been characterized in U.S. Pat. Nos. 5,175,149 and 5,321,011. Broadly, they are pentasaccharide phytohormones comprising methylfucose. A number of these *B. japonicum*-derived LCOs are described: BjNod-V ($C_{18:1}$); BjNod-V ($A_c$, $C_{18:1}$), BjNod-V ($C_{16:1}$); and BjNod-V ($A_c$, $C_{16:0}$), with "V" indicating the presence of five N-acetylglucosamines; "Ac" an acetylation; the number following the "C" indicating the number of carbons in the fatty acid side chain; and the number following the ":" the number of double bonds.

It shall also be understood that compositions comprising different LCOs, are encompassed within the scope of the present invention. Indeed, while the present invention is exemplified with LCOs obtained from *B. japonicum, R. leguminosarum* and *S. meliloti*, and in particular NodBj-V($C_{18:1}$, MeFeu), any LCO produced by a rhizobia which is capable of entering into a nitrogen fixation relationship with a legume (i.e. a member of the Fabiaceae family) is expected to show the same properties as that of the LCOs exemplified herein. It will be clear to the person of ordinary skill that the selection of a rhizobia known to be expressing LCOs at high levels, or known to express an LCO having an effect on a broader spectrum of legumes (such as NGR234) could be advantageous.

It will also be clear that the LCO compositions of the present invention could also comprise more than one signal molecule. Non-limiting examples of such compositions include agricultural compositions comprising in addition to one LCO: (1) at least one additional LCO; (2) at least one plant-to-bacteria signal molecule; (3) gibberellic acid or other agents or compounds known to promote growth or fitness of plants; and mixtures of such compositions (1), (2) or (3).

It shall be clear that having identified new uses for LCO, bacteria could be genetically engineered to express nod genes and used for producing LCOs or for direct administration to the plants and/or seeds.

Thus, while the instant invention is demonstrated in particular with LCOs from *Bradyrhizobium japonicum*, and a selected legume and non-legume crops, the invention is not so limited. Other legume crops, non-legume crops and rhizobial strains may be used using the same principles taught herein. Preferred matching of rhizobia with legume crop groups include, for example:

| rhizobial species | Legume crop group |
|---|---|
| *R. meliloti* alfalfa, | sweet clover |
| *R. leguminosarum* | peas, lentils |
| *R. phaesolii* | beans |
| *Bradyrhizobium japonicum* | soybeans |
| *R. trifolii* | red clover |

As will be apparent to the person of ordinary skill to which the present invention is directed, the growth-stimulating compositions of the present invention can be applied to other crop plants and especially to other warm climate adapted crop plants (plants or crops having evolved under warm conditions [i.e. tropical, subtropical or warm temperature zones] and whose metabolism is optimized for such climates). It should be understood that the photosynthesis-enhancing compositions of the present invention should find utility whenever a particular crop is grown in a condition which limits its growth. For example, whenever a particular plant crop is grown at a temperature (or under environmental parameters) which is below its optimum temperature for photosynthesis and/or growth. Such temperatures are known in the art. For example, optimum temperatures for germination of corn, soybean, rice and cotton are 30° C., 34-36° C., 30-32° C., and 34° C., respectively. The minimum germination temperatures (or base temperatures) for these crops are 9° C., 4° C., 8 to 10° C., and 14° C., respectively, while the maximum germination temperatures are 40° C., 42-44° C., 44° C. and 37° C., respectively. The compositions of the present invention therefore find utility, among other things, in enhancing photosynthesis of warm climate adapted crops when grown at temperatures between their base temperature for photosynthesis and/or growth. The compositions of the present invention find utility in general in enhancing the photosynthesis rate and/or growth of crop plants when grown under conditions which delay or inhibit the photosynthesis and/or growth thereof. Non-limiting examples of such inhibiting conditions (as known from their signalling inhibition in bacteria-legume interactions, their inhibition or delay of the bacteria-plant symbiotic relationship) include pH stress, heat-stress, and water stress.

It will be nevertheless recognized that the compositions and methods of the present invention also can enhance growth of plants grown under optimal conditions.

Thus, the compositions and methods of the present invention should not be limited to plants growing under sub-optimal conditions.

The term "environmental conditions which inhibit or delay the bacterial-plant symbiotic relationship" should be interpreted herein as designating environmental conditions which postpone or inhibit the production and exchange of signal molecules between same and include, without being limited thereto: conditions that stress the plant, such as temperature stress, water stress, pH stress as well as inhibitory soil nitrogen concentrations or fixed nitrogen.

"An agriculturally effective amount of a composition" for increasing the growth of crop plants in accordance with the present invention refers to a quantity which is sufficient to result in a statistically significant enhancement of the photosynthetic rate, growth and/or yield (e.g. protein or grain yield) of the plant crop as compared to the photosynthetic rate and/or growth, and/or yield of the control-treated plant crop. As will be seen below, the photosynthetic and/or yield-promoting activity of the LCOs are observable over a broad range of concentrations. Indeed, LCO photosynthetic rate-promoting activities can be observed at an applied concentration of about $10^{-5}$ to $10^{-14}$ M, preferably about $10^{-6}$ to about $10^{-12}$ M and more preferably about $10^{-6}$ to about $10^{-10}$ M. As shown herein, however, the best of photosynthetic rate-promoting concentration of LCO depends on the growth conditions (e.g. controlled vs environmental) and on the treated plant. A person skilled in the artwill be able to adapt the range or actual concentration of LCO in the composition to satisfy his or her need.

While a direct method of inoculation with the composition of the present invention is preferred, an indirect method can also be employed. During direct inoculation the composition is applied directly onto the plant and preferably by foliar application. This can be accomplished, for example, by spraying the leaves. The indirect method of inoculation would be based on an application of a rhizobia expressing an LCO of the present invention onto the plant.

Foliar applications such as spray treatments of leaves are well-known in the art. Of course, the method of administration of a composition of the present invention to the leaves can be adapted by a skilled artisan to meet particular needs.

The time at which the compositions and methods of the present invention are effective in enhancing a plant's photosynthetic, and/or growth, and/or yield thereof, in accordance with the present invention is from as soon as a leaf is present until physiological maturity of the plant. More particularly, the administration of the composition should occur between the seedling stage and the late pod filing stages. Thus, the administration can occur during the seedling, flowering and pod filing stages.

The recitation "short season condition" refers herein broadly to temperatures of the middle and temperate zones and shorter. Typically, the active growing season is around ½ to ⅔ of the year. Short season conditions broadly refers to a frost-free period of less than half the year, often on the order of 100 frost-free days.

By "nodulation gene-inducing" or "nodgene-inducing" is meant bacterial genes involved in nodule establishment and function.

BRIEF DESCRIPTION OF THE DRAWINGS

Having thus generally described the invention, reference will now be made to the accompanying drawings, showing by way of illustration a preferred embodiment thereof, and in which.

Figure 1:
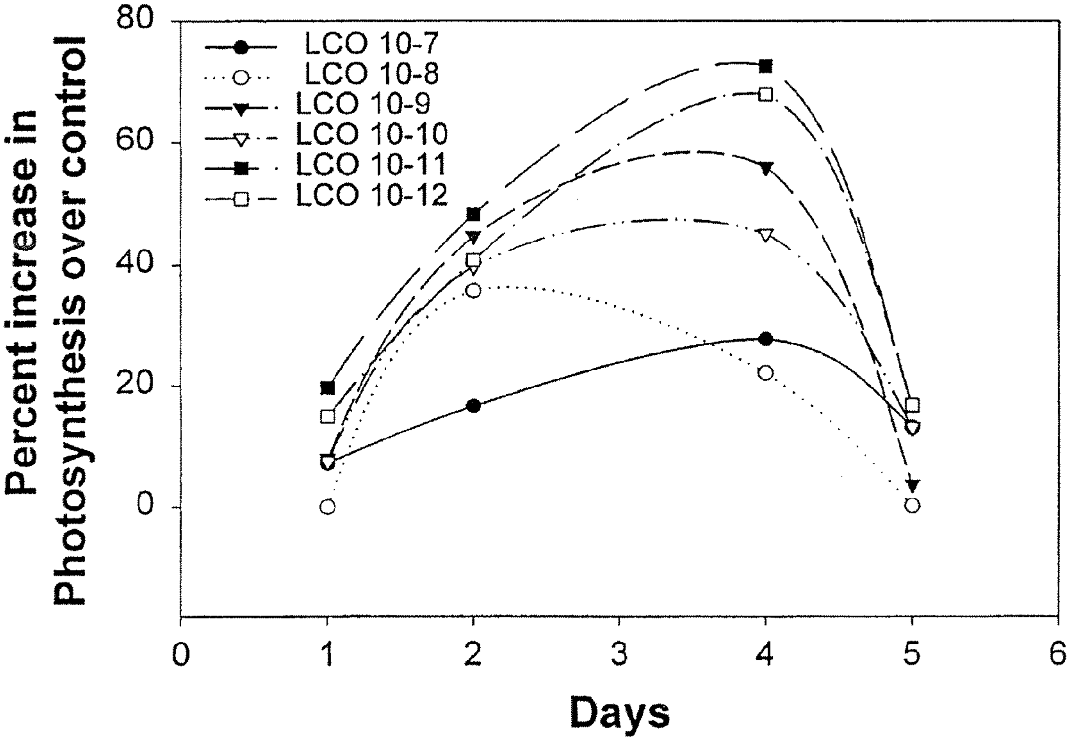
FIG. 1 shows the effect of lipo-chitooligosaccharide Nod Bj V(C18:1, MeFeu) over time on percent increase in photosynthetic rate of soybean (cv Bayfield) under greenhouse conditions.

Other objects, advantages and features of the present invention will become more apparent upon reading of the following non-restrictive description of preferred embodiments with reference to the accompanying drawing which is exemplary and should not be interpreted as limiting the scope of the present invention.

DESCRIPTION OF THE PREFERRED EMBODIMENT

The research reported herein was conducted to study the effects of foliar applications of LCO on the photosynthetic rates of a host plant (soybean) and non-host plants (rice, melon, canola, and corn) under green house conditions. Also, field experiments were conducted to study the effect of LCO application on photosynthesis by corn, grape, apple and soybean. Field experiments were also carried through to the examination of yield and yield components.

During the course of work on the ability of LCOs to stimulate seed germination of plants, it was observed that seedlings left exposed to a composition comprising LCOs, following germination, continued to grow faster. The possibility that an application of LCO to leaves of seedlings would increase their photosynthetic rates, leading to faster growth rates, was thus formerly tested. It was thereby shown that LCOs increase the photosynthetic rates and/or yield of plants in general, as exemplified both under greenhouse conditions and under field conditions with a number of evolutionary divergent plants.

Lipochitin oligosaccharide (LCO) nod Bj V (C18:1, MeFeu) isolated from *Bradyrhizobium japonicum* 532C was evaluated for its effect on the photosynthetic rates of a number of crop plants belonging to diverse botanical families: soybean (Fabaceae) corn, rice (Poaceae), melon (Cucurbitaceae), canola (Brassicaceae) apple (Rosaceae) and grape (Vitaceae). LCO enhanced photosynthesis of all the plants tested. However, the extent of the responses are dependent on the plant species and the concentration LCO used. Under green house conditions soybean (cv Bayfield) showed the largest increase in photosynthesis due to LCO spray; on an average there was a 50% increase in photosynthetic rate. As LCO application resulted in increased stomatal aperture without any increase in leaf internal $CO_2$ concentration, the data indicate that there was an increase in $CO_2$ uptake by chloroplasts, which lead to increased stomatal opening. LCO sprayed plants had more leaf area and dry weight than water sprayed controls. Underfield conditions LCO spray was tested on soybean, corn, apple and grape plants. In the case of soybean the spray applied at the seedling, flowering and pod-filling stages, resulted in increased branch number, leaf area, pod number, plant dry matter and grain yield. LCO application enhanced grain yield by 33-44%. The data illustrate that LCOs can be used to increase the productivity of a wide range of crops.

The present invention is illustrated in further detail by the following non-limiting examples.

Example 1

Production Extraction and Purification of Lipo-Chitooligosaccharides (LCOs)

Bacterial Culture

*Bradyrhizobium japonicum* (strain 532C) was grown at 28° C. in yeast mannitol medium (YEM) (Mannitol 10 g, $K_2HPO_4$ 0.5 g, $MgSO_4$ $7H_2O$ 0.2 g, NaCl 0.1 g, yeast extract 0.4 g and distilled water 1000 mL), pH 6.8, shaken at 150 rpm until the $OD_{620}$ reached 0.4-0.6 (4-6 days) in the dark. Thereafter, 2 L of bacterial subculture was started by inoculating with material from the first culture (5 mL of the first culture per 250 mL ofYEM media), for 5-7 days ($OD_{620}$-0.8-1.0), as above. At this stage, 0.25 mL of 50 μM genistein (in methanol) was added to each 250 mL of bacterial subculture (genistein concentration of 5 μM) and the culture was incubated for 48-96 hours.

Extraction of LCOs

Two liters of bacterial subculture were phase-partitioned against 0.8 L of HPLC-grade 1-butanol by shaking overnight. The upper butanol layer was transferred to a 1 L evaporation flask and concentrated to 2-3 mL of light brown, viscose material with a rotary evaporator operated at 80° C. (Yamota RE500, Yamato, USA). This extract was resuspended in 4 mL of 18% acetonitrile and kept in the dark at 4° C. in a sealed glass vial until use. HPLC analysis (Waters, Mass., USA) was conducted with a Vydac C18 reversed-phase column (Vydac, Calif., USA; catalogue #218TP54) with a flow rate of 1.0 mL $min^{-1}$ and a Vydac guard column (catalogue #218GK54). As a baseline 18% acetonitrile ($AcN/H_2O$; w/w) was run through the system for at least 10 min prior to injection. The sample was loaded and isocratic elution was conducted with 18% AcN for 45 min to remove all non-polar light fractions. Thereafter, gradient elution was conducted for 90 min. with 18-82% AcN. The LCO was eluted at 94-96 min of HPLC run time.

The chemical identity of the LCO was confirmed by mass spectrometer (MS-MS) analysis to be Nod Bj V (C18:1 MeFeu) (R. Carlson, Complex Carbohydrate Research Centre, University of Georgia, Athens, USA) and by root hair deformation assay (Prithiviraj et al., 2000).

Plant Material

Briefly, seeds of soybean (cv AC Bravor) were surface sterilized with 2% sodium hypochlorite for 2 min and washed with at least four changes of sterile distilled water. The seeds were then placed on 1.5% water agar (20 mL) in 9 cm diameter Petri dishes (two seeds per plate). The Petri dishes were incubated in the dark at 25° C. for 7-8 days; during this time the seeds germinated and developed tap and lateral roots on the agar surface. Lateral roots with abundant root hairs, which could be easily distinguished by the fluffy appearance they imparted to the lateral roots, were excised with a sterile scalpel. These lateral roots were placed on sterile grease free glass slides containing 40-60 μL of LCO solution. The slides were then placed in a moist chamber and incubated for 24 h at 25° C. in the dark. At the end of the incubation time the slides were removed and the roots were fixed in a staining solution [methylene blue (0.02% w/v)+glycerol (20% v/v)+phenol (10% w/v)]. Slides were observed under a light microscope for root hair deformation.

Example 2

LCO Treatment and Data Collection for the Greenhouse Experiments

Plant Treatment

Soybean (cv Bayfield) seeds were surface sterilized with 2% sodium hypochlorite for 3-4 minutes, washed with several changes of sterile distilled water and germinated in plastic trays containing sterile vermiculite. Seedlings at the two-leaf stage, about seven days of planting, were transplanted into 15 cm plastic pots containing promix (Premier Brands Inc., New Rochelle, N.Y., USA). Pots were placed in a greenhouse maintained at 25±2° C. with a day/night cycle of 16/8 h. Plants were watered as required.

Seeds of rice (Oryza sativa cv Cypress), canola (*Brassica napus* cv Springfield), corn (*Zea mays* cv Pioneer 3921) and melon (*Cucumis melo* cv Nova) were surface sterilized with 2% sodium hypochlorite for 3-4 min, washed with several changes of sterile distilled water and planted in plastic pots (15 cm dia) containing promix (Premier Brands Inc., New Rochelle, N.Y., USA).

LCO Treatment

Concentrations of LCO ($10^{-6}$ M-$10^{-12}$ M) were made with distilled water containing 0.02% Tween 20. A control treatment, containing 0.02% Tween 20, but no LCO was also applied. Since the rates of growth and development differed among the plant species used in the experiments, spray treatment was conducted at different times after planting In general, the spray was applied when the plants were big enough to allow easy measurements of leaf photosynthetic rates. The following are the ages of the plants when the sprays were conducted: soybean 21 days after planting (DAP), corn 25 DAP, rice 45 DAP, melon (35 DAP) and canola 30 DAP. The plants were sprayed with LCO solutions until dripping. The sprays were applied with an atomizer (Nalgene, USA). Each plant required 2-3 mL of spray solution. Each treatment was replicated at least five times and organized on the green house bench in a randomized complete block design. Each experiment (with each crop species) was repeated at least twice.

Data Collection

Photosynthesis was recorded every 24 h using a Li-Cor 6400 portable photosynthesis system (Li-Cor Inc., Lincoln, Nebr., USA) for 6 days. In the case of soybean the photosynthesis in the second nodal leaf from the top was recorded while in the other species used in the photosynthetic rate was measured for the top-most fully expanded leaf. Soybean plants were harvested after seven days of LCO treatment and dried at 80° C. for 48 h. Data were analyzed with the Statistical Analysis System (SAS Inc., N.C., USA). Percent increase in photosynthesis over the control was calculated. Multiple means comparisons were conducted with an ANOVA protected LSD test, thus, the LSD test was not performed if the ANOVA test did not indicate the presence of differences due to treatment.

Example 3

Field Experiments

Year 1999

Soybean

The soybean experiment was conducted at the Lods Agronomy Research Centre, McGill University, Macdonald Campus, Ste-Anne-de-Bellevue, Quebec, Canada during the period June to September, 1999. A randomized complete block design with three blocks was followed. The plot size was 2×4 m with a row to row spacing of 25 cm and 10 cm between plants within a row. Seeds of soybean (cv OAC Bayfield), treated with commercial *Bradyrhizobium japonicum* inoculant (Bios Agriculture Inc., Quebec, Canada) at the rate of 3 g per kilogram of seed, were hand planted.

At 25 days after planting twenty plants in each plot were randomly marked and sprayed until dripping with LCO solutions ($10^{-6}$, $10^{-8}$ and $10^{-10}$M) containing 0.02% Tween 20 with a hand sprayer. The plants on either side, within the row, of the marked plants were also sprayed. A second spray was carried out at flowering stage and a third spray at pod filling.

Apple, Grape and Corn

These experiments were conducted at the horticultural research facility of McGill University, Ste-Anne-de-Bellevue, Quebec, Canada during July 2000. LCO of different concentrations ($10^{-8}$, and $10^{-10}$M) were prepared as described above. Branches of apple (cv Empire) and Grapes (cv De Chaunac) were sprayed with LCO and the photosynthesis was observed every 24 h for five days with a Li-Cor 6400 portable photosynthesis system (Li-Cor Inc., USA). Each treatment was applied to three branches from the same plant. Care was taken to ensure that the branches were on the same level and orientation. Part of each branch was sprayed with LCO and the remaining part served as a control. The control portion of the branch was sprayed with distilled water containing the same amount of Tween 20 as the LCO treatment solution. Observations were taken on 15 leaves per replicate for each treatment. For both apple and grape the entire procedure was repeated twice on two different plants.

Single row corn plots (Pioneer 3921) were established during the 1999 and 2000 cropping seasons. The rows were 75 cm apart and their was an average of 20 cm between plants. The plants were sprayed at 40 DAP. Photosynthetic rates were recorded each day for 5 days after spray application. However, multiple sprays of LCO on corn were not possible due to limitations of LCO supplies, and because only single row plots were used yields were not recorded.

Field Data Collection

As with the indoor experiments, photosynthetic readings were taken every day for five days after the application of LCO. For soybean additional developmental and agronomic data were collected. The first harvest was conducted at 25 days after the first spray treatment. Five plants were harvested from each plot and the following growth variables were analyzed: plant height, number of branches, number of leaves, leaf area, number of flower clusters, number of pods, number of nodules, dry weights of leaves, stem and roots. The final harvest was conducted after physiological maturity of the plants (Fehr et al., 1971); at this time the remaining fifteen treated plants from each plot were harvested and data on number of branches, number of pods, number of seeds and grain yield per plant was collected.

Example 4

Effect of LCOs on the Photosynthetic Rate of Soybean and Non-Legumes Under Greenhouse Conditions LCO spray increased the photosynthetic rate of soybean even at very low concentrations (Table 1).

TABLE 1

Effect of lipo-chitin oligosaccharide (Nod Bj V (C18:1, MeFeu)) on photosynthesis (μmol $m^{-2}$ $sec^{-1}$) of soybean under greenhouse conditions.

| | Days after treatment | | | | |
|---|---|---|---|---|---|
| Treatment | 1 | 2 | 4 | 5 | 6 |
| Control | 11.2 d@ | 8.1 c | 10.1 d | 12.1 c | 10.4 a |
| $10^{-6}$ | 14.9 ab | 12.1 a | 16.2 a | 16.7 ab | 13.1 a |
| $10^{-7}$ | 12.1 cd | 9.1 bc | 12.9 bcd | 14.1 bc | 11.1 a |
| $10^{-8}$ | 13.8 b | 8.1 bc | 12.3 cd | 16.4 ab | 10.3 a |
| $10^{-9}$ | 15.8 a | 8.4 bc | 15.7 ab | 17.5 ab | 11.2 a |
| $10^{-10}$ | 13.6 bc | 8.7 bc | 14.6 abc | 16.9 ab | 11.2 a |
| $10^{-11}$ | 14.0 b | 8.7 bc | 17.4 a | 17.9 a | 12.5 a |
| $10^{-12}$ | 15.0 ab | 10.3 ab | 16.9 a | 17.0 ab | 12.0 a |
| LSD ($p < 0.05$) | 1.67 | 2.24 | 3.15 | 3.78 | 2.87 |

@means with in the same column, followed by the same letter are not significantly different
($p < 0.05$) by ANOVA protected LSD test.

Figures 2A, 2B, 2C, 2D:
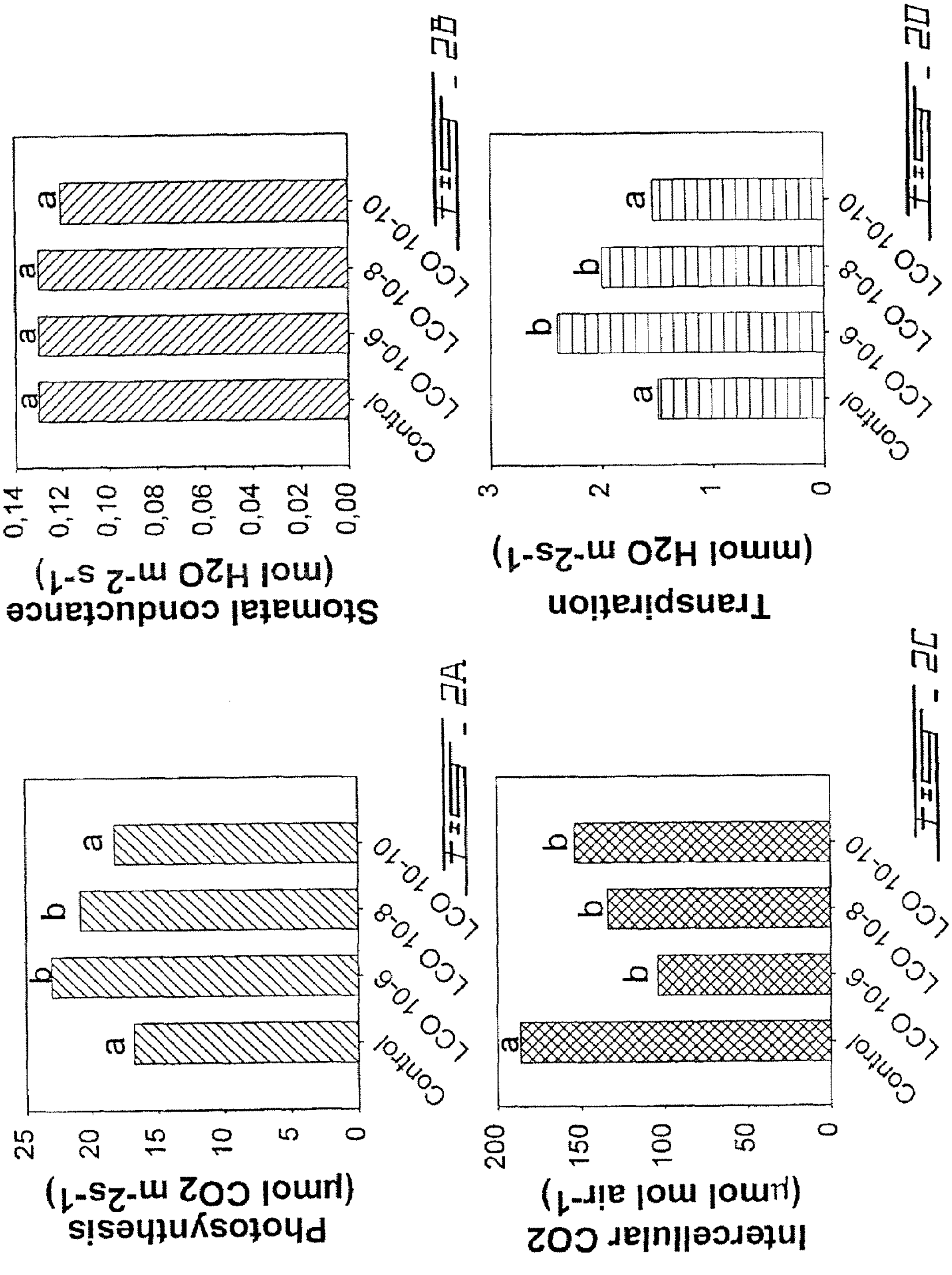
FIG. 2 shows the effect of lipo-chitooligosaccharide Nod Bj V(C18:1, MeFeu) on photosynthetic rate of corn (cv Pioneer 3921) (at the time of maximum effect, 2 days after treatment)
Figures 3A, 3B, 3C, 3D:
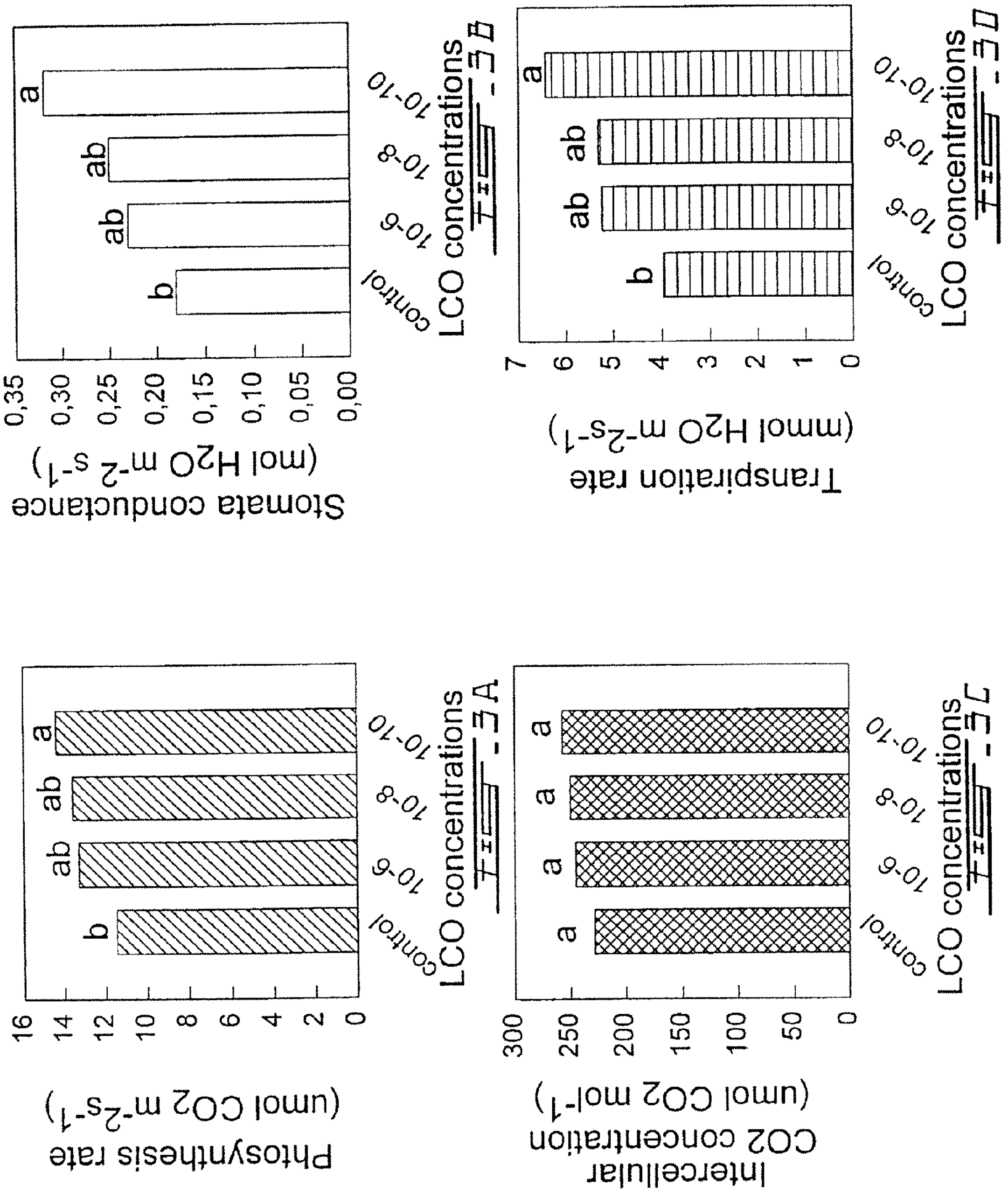
FIG. 3 shows the effect of lipo-chitooligosaccharide Nod Bj V(C18:1, MeFeu) on photosynthetic rate of rice (cv Cypress) (at the time of maximum effect, three days after treatment)

The photosynthesis rate increased from day 1 up to day 4 after which it decreased and by day 5 it generally reached levels not different from the control plants. However, the maximum increase in photosynthesis was observed on day four in most treatments. Percent increase in photosynthesis over the control varied with the concentration of LCO spray (FIG. 1). LCO at $10^{-11}$ M caused the greatest increase in photosynthetic rate followed by $10^{-12}$ M, with these maxima occurring at four days after treatment, while other concentrations caused more sustained increases in photosynthesis, that remained higher than the control for more extended periods of time. LCO treatments caused an increase in the leaf area and dry weight of soybean at seven days after treatment (FIGS. 2 and 3). shoot dry weights of treated plants were statically ($p<0.05$) higher than those of the control plants, while leaf areas were only increased numerically ($p=0.09$).

Figures 4A, 4B, 4C, 4D:
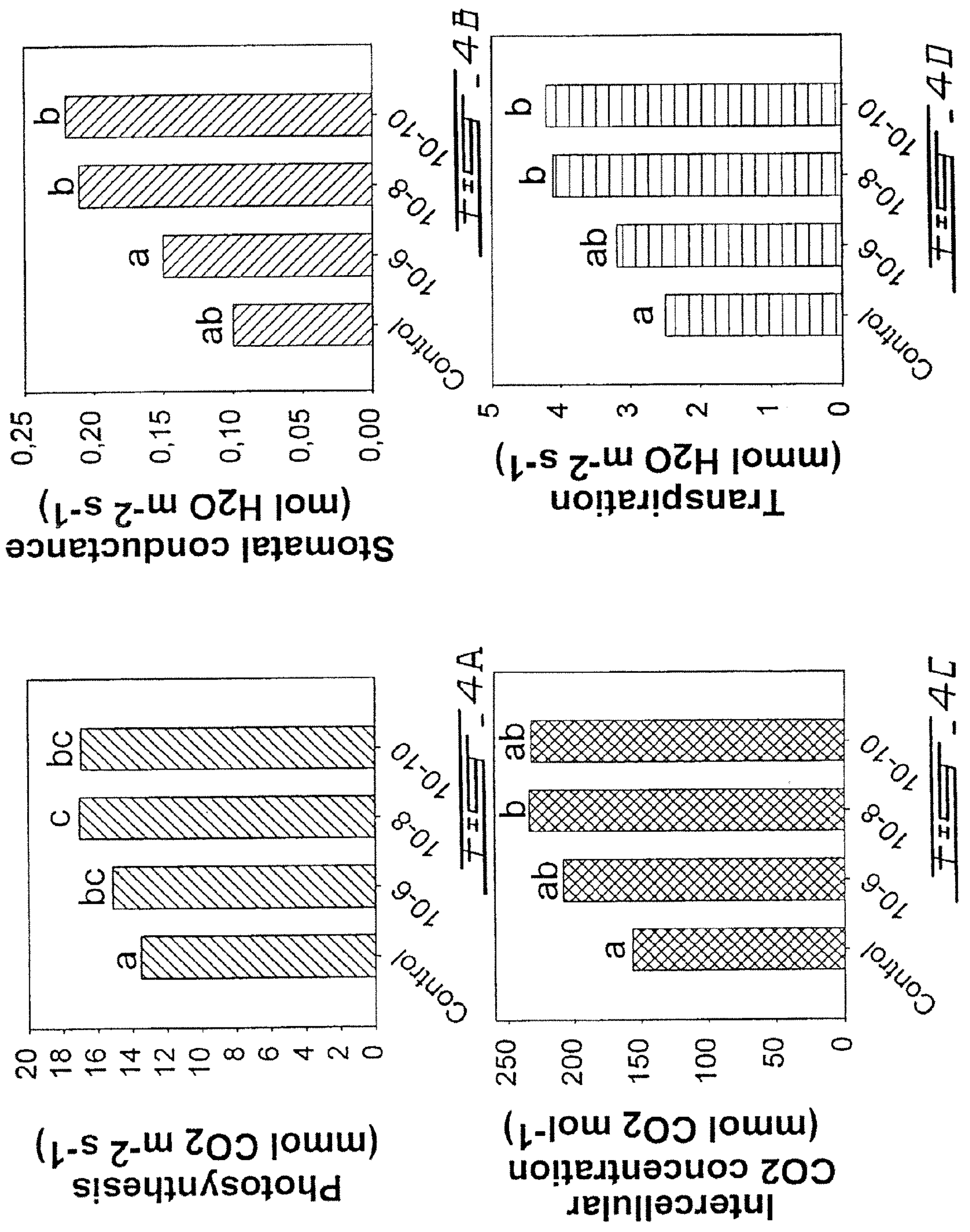
FIG. 4 shows the effect of lipo-chitooligosaccharide Nod Bj V(C18:1, MeFeu) on photosynthetic rate of canola (cv Springfield) (at the time of maximum effect, two days after treatment)
Figure 5B:
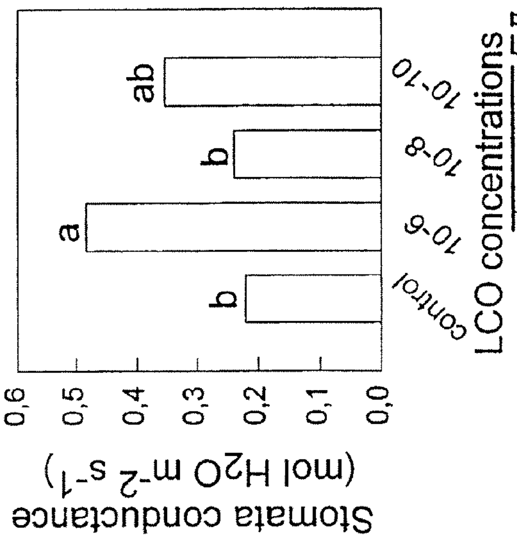
FIG. 5 shows the effect of lipo-chitooligosaccharide Nod Bj V(C18:1, MeFeu) on photosynthetic rate of melon (cv Nova) (at the time of maximum effect, three days after treatment)
Figure 5A:
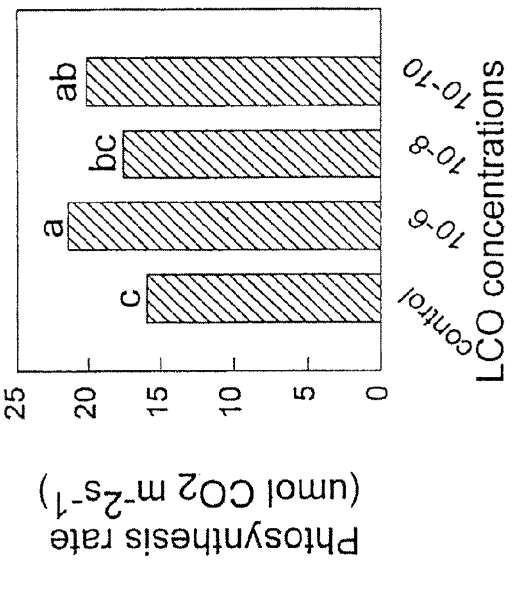
Figure 5D:
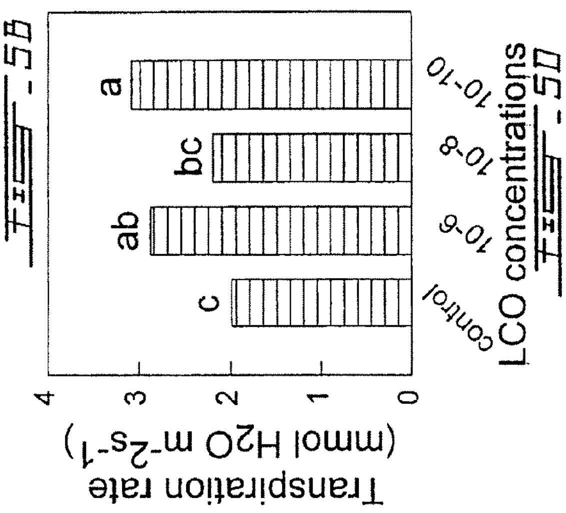
Figure 5C:
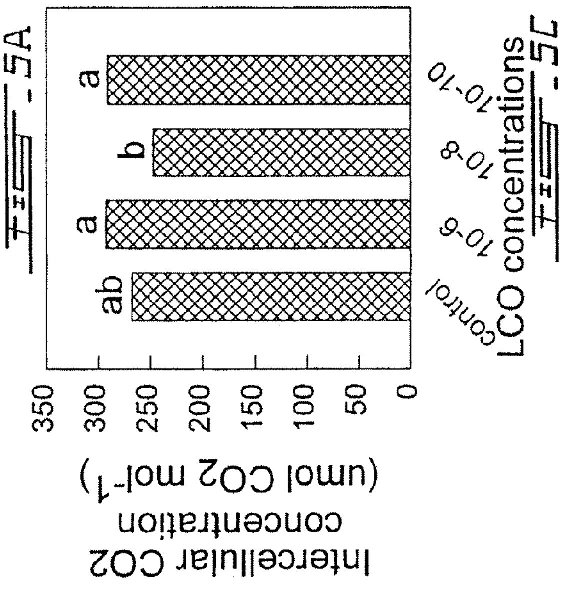

LCO treatment also enhanced the photosynthetic rates of non-legumes: corn (FIG. 4), rice (FIG. 5), canola (FIG. 6) and melon (FIG. 7). It was evident that the days for maximum increase and the most effective concentration of LCO differed among the species. In general a 10-20% increase in photosynthesis was common. For the $C_3$ plants (rice, melon, canola) the increased in photosynthetic rates were always accompanied by a concomitant increases in stomatal conductance and transpiration while the intercellular $CO_2$ concentration was unaffected by the treatments. For corn (a $C_4$ plant) LCO application increased photosynthetic rate, decreased leaf internal $CO_2$ concentration and did not significantly alter stomatal aperture, These data argue that the increase in photosynthetic rate was due to an increase in photosynthetic uptake of $CO_2$ inside the leaf, which, in the case of $C_3$ plants, triggered an increase in stomatal aperture. Had it been the case that increased stomatal aperture was the primary cause of the increased photosynthetic rates one would have expected increases in the internal $CO_2$ concentration of the leaf (Morison, 1998).

Example 5

Effect of LCOs on the Photosynthetic Rate, Growth and Yield of Soybean and Bon-Legumes Grown Under Field Conditions (Year 1999)

Grape, Apple and Corn

Figures 6A, 6B, 6C, 6D:
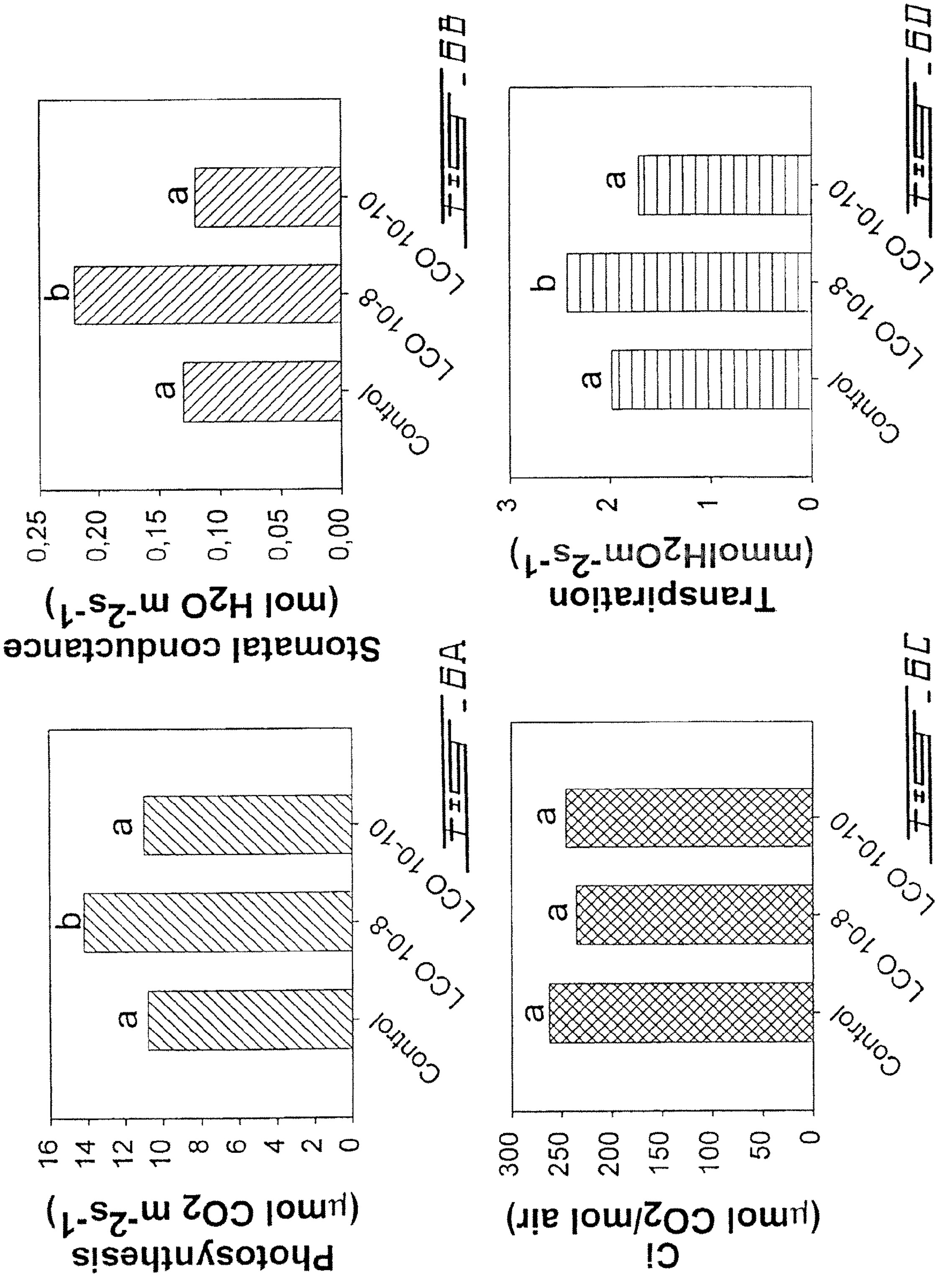
FIG. 6 shows the effect of Lipo-chitooligosaccharide Nod Bj V(C18:1, MeFeu) on photosynthetic rate of apple (cv Empire) under field conditions (at the time of maximum effect, five days after treatment)
Figure 7A:
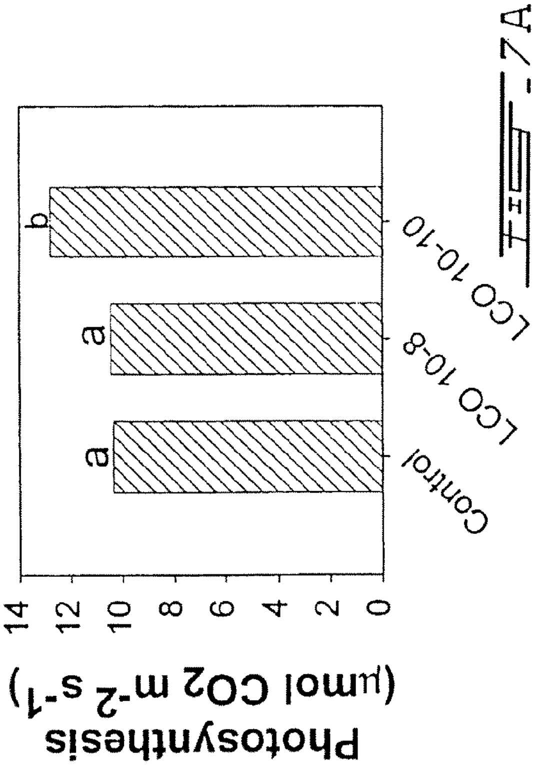
FIG. 7 shows the effect of lipo-chitooligosaccharide Nod Bj V(C18:1, MeFeu) on photosynthetic rate of grape (cv Du Chaunac) under field conditions (at the time of maximum effect, three days after treatment)
Figure 7B:
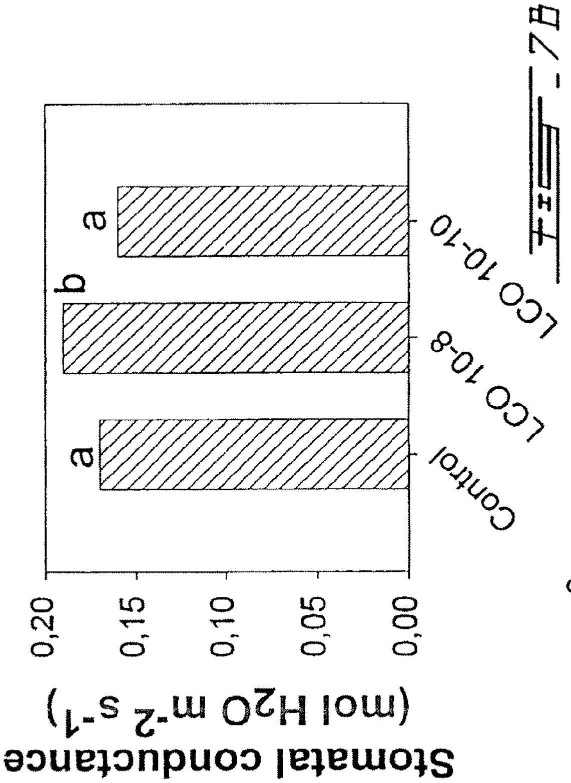
Figure 7C:
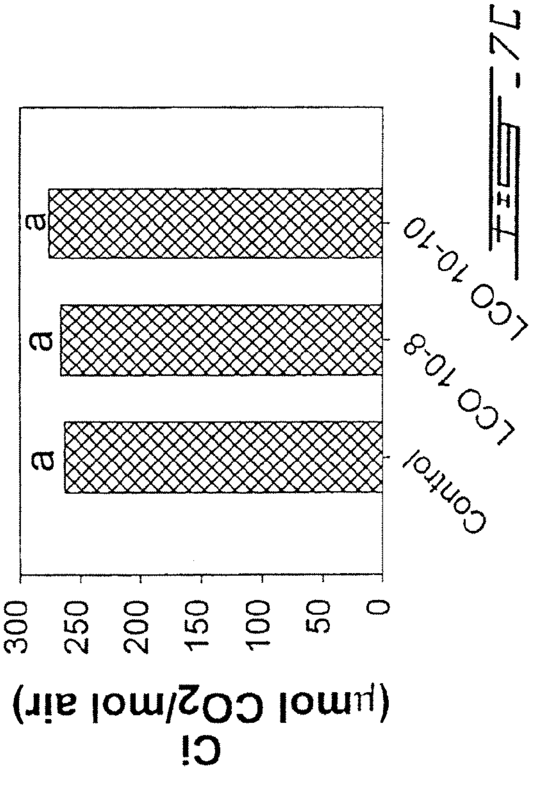
Figure 7D:
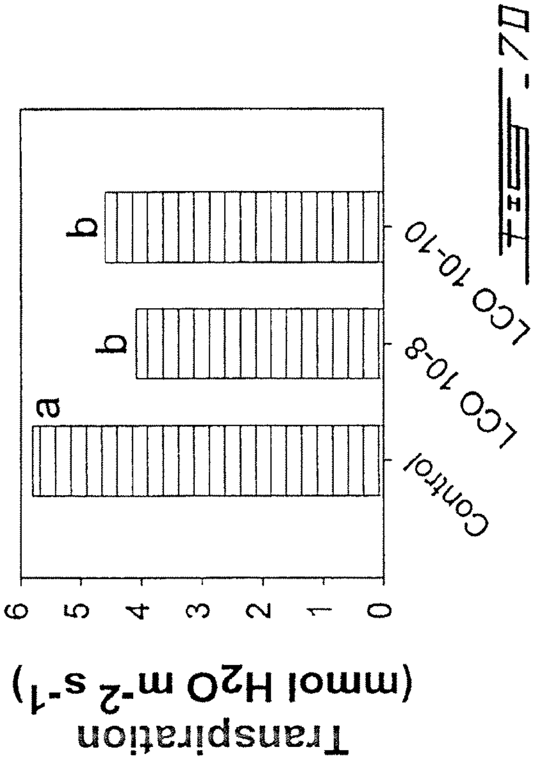
Figure 8A:
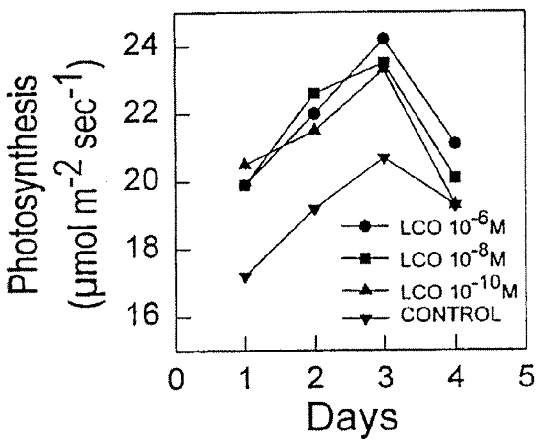
FIG. 8 shows the effect of Lipo-chitooligosaccharide Nod Bj V(C18:1, MeFeu), over time, on photosynthetic rate of soybean (cv Bayfield) under field conditions.
Figure 8B:
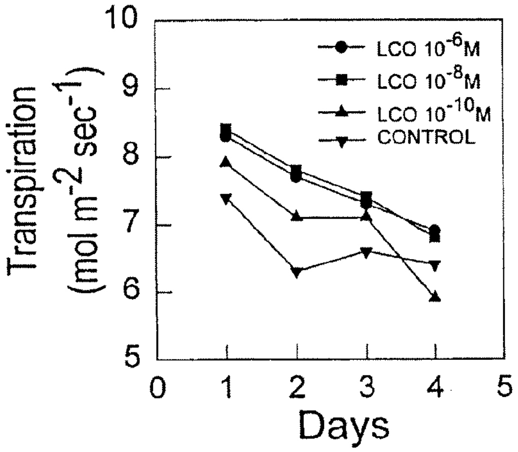
Figure 8C:
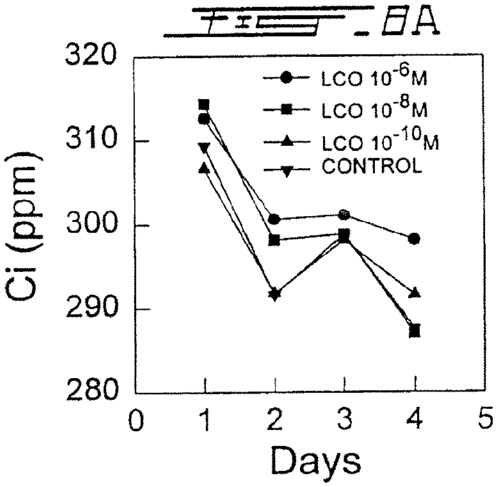
Figure 8D:
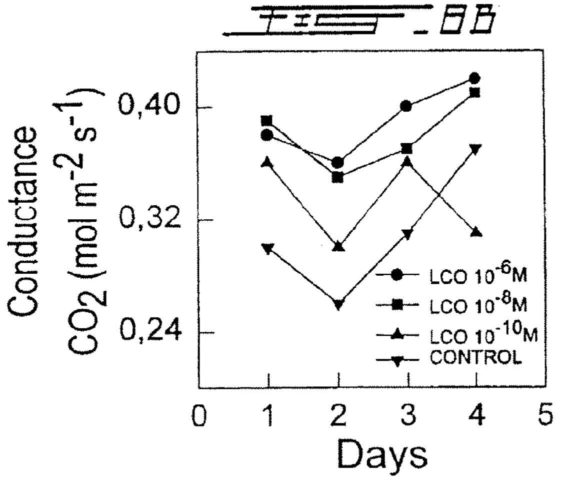
Figure 8E:
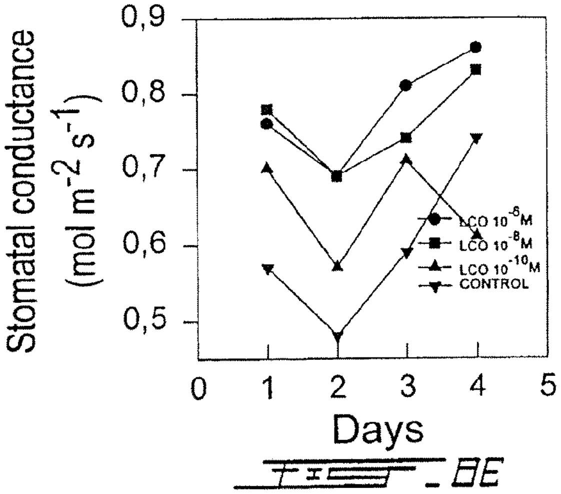
Figure 9A:
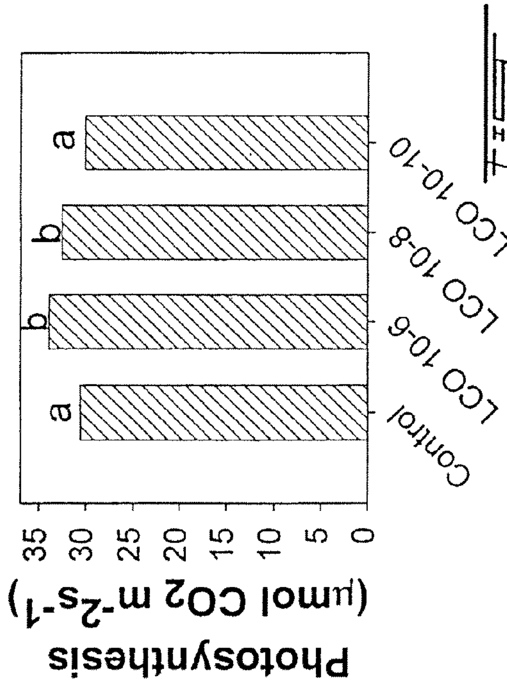
FIG. 9 shows the effect of Lipo-chitooligosaccharide Nod Bj V(C18:1, MeFeu) on photosynthesis of corn under field conditions (at the time of maximum effect, two days after treatment).
Figure 9B:
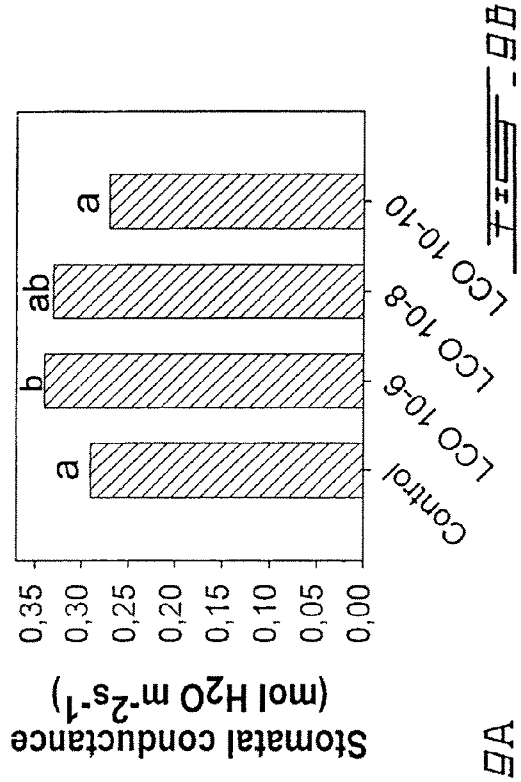
Figure 9C:
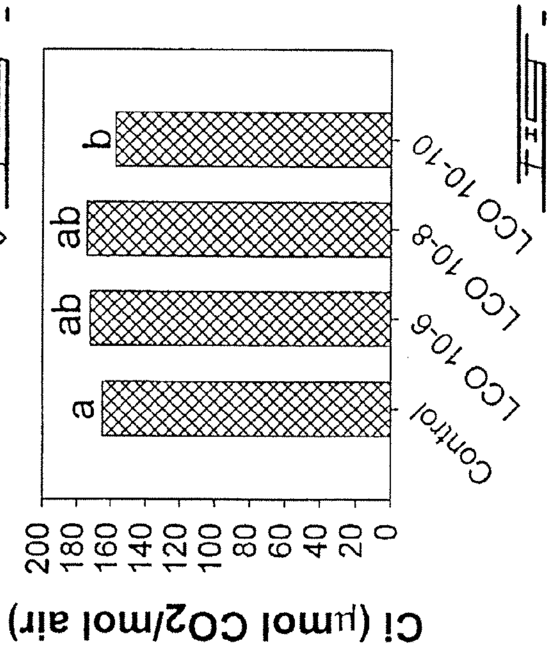
Figure 9D:
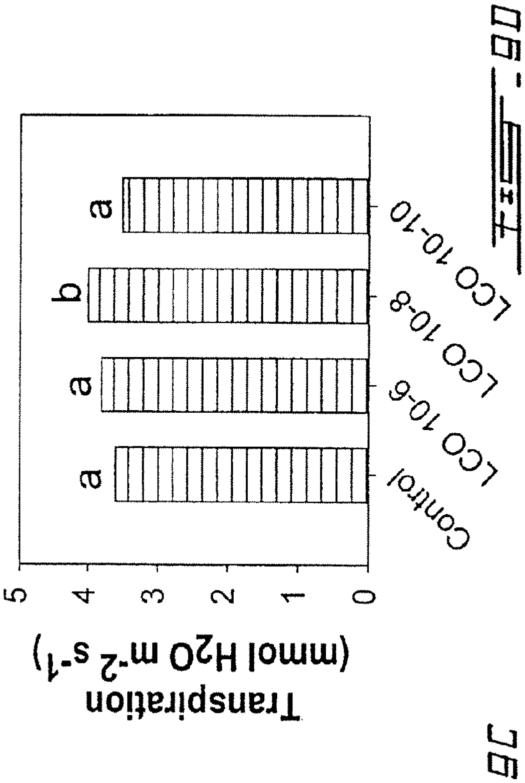

LCO spray also caused increases in the photosynthetic rates of field-grown apple and grape (FIGS. 8 and 9). In case of apple, photosynthesis increase peaked at five days after treatment; the $10^{-8}$ M LCO treatment resulted in a photosynthetic rate of 14.1 μmol $CO_2$ $m^{-2}s^{-1}$, while the rate was 10.8 μmol $CO_2$ $m^{-2}$ $s^{-s}$ for the control. As with the other crops there were increases in stomatal conductance without any effect on the Ci. LCO treatment also increased transpiration (FIG. 6). In grapes, the greatest increase in photosynthetic rate occured three days after treatment with the $10^{-10}$ M LCO treatment, and this resulted in a concomitant increase in stomatal conductance. LCO application increased the photosynthetic rate of field grown corn by a maximum of approximately 10% (FIG. 10) at two days after treatment application. While LCO application did cause reduced Ci levels in the greenhouse ($p=0.05$) there was no such effect on Ci in field grown plants.

Soybean

In general, the photosynthetic responses of soybean in the field were similar to those observed under greenhouse conditions. LCO treatment resulted in increases in the photosynthetic rates from day one to day four after application. The most effective concentration was $10^{-6}$ M, which resulted in a photosynthetic rate of 24 mmol $m^{-2}$ $sec^{-1}$ on day three as compared to 20 mmol $m^{-2}$ $sec^{-1}$ for the control (FIG. 10). The increase in photosynthetic rate was accompanied by increases in stomatal conductance; again the $10^{-6}$ M LCO treatment resulted in the highest stomatal conductance values. However, the effect of LCO in the field grown plants were less pronounced than for green house gown plants and required higher concentration for better effects. The requirement for higher concentrations may have been due to leaf anatomical differences; field grown plants usually have thicker cuticles than green house grown plants. It might also have been the case that epiphytic microorganisms, or the leaves themselves, may have produced chtinases that degraded the LCO. Given the likelihood of lower levels of microbial activity under greenhouse conditions, both of these could have contributed to the need for higher LCO concentrations in the field than the greenhouse. The lower degree of response under field conditions may have been due the greater environmental variability, and increased likelihood of at least some other stresses imposing limitations, at least some of the time, under field conditions. Raschke et al., (1979) observed differences in stomatal sensitivity to $CO_2$ level between green house and field grown maize. Similarly, Talbott et al. (1996) showed differences in stomatal sensitivity to $CO_2$ between growth cabinet and greenhouse plants. LCO treatment resulted in increased transpiration, probably due to increased stomatal aperture.

LCO spray resulted in increased growth of soybean plants. There were increases in the following growth variables: number of branches, number of leaves and leaf area. However, plant height was not affected by LCO treatment. There also increases in the yield variables number of pod clusters per plant, number of pods and total number of seeds per plant. The latter resulted in increases in seed yield that ranged from 33.7 to 44.8% (Table 2).

TABLE 2

Effect of lipo-chitin oligosaccharide (Nod Bj V (C18:1, MeFeu)) leaf area and shoot dry weight of soybean under greenhouse conditions

| Treatment | Leaf area ($cm^2$) | Shoot dry weight (mg) |
|---|---|---|
| Control | 188.0 ab@ | 951.6 b |
| $10^{-6}$ | 223.6 a | 1065.8 ab |
| $10^{-7}$ | 193.6 ab | 1135.2 a |
| $10^{-8}$ | 217.6 ab | 1095.7 ab |
| $10^{-9}$ | 194.3 ab | 999.9 ab |
| $10^{-10}$ | 195.3 b | 1012.3 ab |
| $10^{-11}$ | 202.6 ab | 931.6 b |
| $10^{-12}$ | 230.3 a | 1060.8 ab |
| LSD ($p < 0.05$) | 36.2 | 168.3 |

@means with in the same column, followed by the same letter are not significantly different ($p < 0.05$) by ANOVA protected LSD test.

more opened there were concomitant increases in transpiration for the leaves of LCO treated plants. These results were similar to those observed for glycinebetanine application (Rajasekaran et al., 1997; Makela et al., 1999). Foliar application of glycinebetanine enhanced net photosynthesis and water use efficiency and mitigated drought and salinity stress. Increased stomatal conductance have been positively correlated with the yield in a number of crops and it has been suggested that selection for increased stomatal conductivity will result in enhanced yields (Lu et al., 1998; Morrison et al., 1999). The link between stomatal aperture and photosynthetic rate would seem to apply in the case of the $C_3$ plants tested here, although, it is clear that, the case of LCO application, the more open stomata were the result of greater photosynthetic $CO_2$ uptake by the chloroplasts, and not the primary cause of increased photosynthetic rates.

Dinitrogen fixation is energy intensive process. About 10-20% of the photosynthates of a nitrogen-fixing legume are consumed in $N_2$ fixation. If this were not compensated by an increase in net photosynthesis it would lead to reduction in the crop yield as compared to plants receiving nitrogen fertilizer, and such photosynthetic compensation has been demonstrated (Imsade, 1983). However, mechanisms by which plants compensate for the increased demand during this, and other, plant-microbe interactions are unknown. Our work suggests that this might be controlled by the LCO bacteria-to-plant signal molecules. Several lines of evidence suggest that nodulated soybean plants have higher net photosynthetic rates than those acquiring their nitrogen from mineral forms available in the rooting medium (Imsande, 1989a,b). This might be brought about either by increase in photosynthesis due to improved efficiency in the dark reactions or by enhanced efficiency of the photosystems as reported by Maury et al. (1993), or both.

Recently, Phillips et al. (1999) isolated lumichrome, a breakdown product of riboflavin, in the rhizosphere of alfalfa plants during early nodulation and showed that it caused increased respiration and photosynthetic carbon fixation. In

TABLE 3

Effect of lipo-chitin oligosaccharide (Nod Bj V (C18:1, MeFeu)) on growth and yield of soybean under field conditions.

| Treatment | Plant height (cm) | No. Branches/ Plant | No. Leaves/ Plant | Leaf area/ Plant ($cm^2$) | No. Nodules/ Plant | Root Dry weight/ plant (gm) | Shoot dry weight/ Plant (gm) | No. Pod clusters/ Plant | No. Pods/ Plant | No. seeds/ Plant | Seed yield/ Plant (gm) |
|---|---|---|---|---|---|---|---|---|---|---|---|
| Control | 85.2 | 4.4 | 22.1 | 1388.1 | 60.1 | 2.0 | 19.0 | 18.6 | 33.5 | 80.9 | 15.7 |
| LCO $10^{-6}$ M | 78.5 | 4.2 | 29.4 | 2306.3 | 63.5 | 3.0 | 24.7 | 24.3 | 42.9 | 104.7 | 22.1 |
| LCO $10^{-8}$ M | 85.8 | 5.1 | 25.4 | 2120.4 | 84.6 | 2.3 | 23.7 | 24.8 | 42.4 | 106.3 | 21 |
| LCO $10^{-10}$ M | 83.5 | 3.4 | 22.2 | 1513.1 | 68.3 | 2.3 | 19.8 | 28.3 | 48.0 | 118.1 | 22.6 |
| Contrast ($p < 0.05$): LCO Vs Control | NS | * | * | ** | NS | * | * | * | * | * | * |

The results presented demonstrate that foliar application of LCO Nod Bj (C1:18 MeFeu) causes enhanced photosynthesis in both host and non-host plants. For $C_3$ plants the increase in photosynthesis was always accompanied with increases in stomatal conductance, although without change in Ci values, while for corn (a $C_4$ plant) the stomatal aperture did not increase and the Ci values declined under green house conditions. In both cases the data indicate that increases in photosynthesis due to LCO treatment is due to more efficient $CO_2$ uptake inside the leaf. For the $C_3$ plants this lead to increased stomatal aperture. Because the stomata of the $C_3$ plants were an earlier experiment we observed enhanced germination and early growth of diverse crop plants due to LCO treatment (unpublished results) and this led us to hypothesize that LCO improves early growth through increased photosynthesis. The results of the present experiment support the above hypothesis. Identification of specific high affinity receptors for LCOs remains elusive. However, two class of receptors for LCO have been characterized recently (Stacey et al., 2000; Bono et al., 1995; Gressent et al., 1999). This led us to hypothesize that one of these receptors is associated with the nodulation process and the other with a more generalized process that triggers the growth machinery of plants when exposed to chitin and related compounds, such as LCOs. The observation that this stimulation occurred in such a wide variety of angiosperms (the work reported here shows effects in five plant families, all angiosperms: Poaceae, Fabaceae, Brassicaceae, Rosaceae, Vitaceae) suggests that this LCO response mechanism is at least as old as the angiosperms. There are several reports of the presence of nod factor responsive genes in non-legumes such as rice (Kouchi et al. 1999; Reddy et al 1998). These may play a role in the detection of, and response to, plant pathogens, many of which contain chitin in their cell walls. Presumably, more vigorous growth is a response to the presence of a detected pathogen. There are several reports of enhanced photosynthesis due to fungal pathogens (Ayers, 1979; 1981) this might be due to the stress responses of the plant and could be mediated by cell wall fragments that are chitin oligomers.

The phenomenon of enhanced photosynthesis and yield due to application of LCO, as observed in this study, might explain, at least in part, the increased productivity of legume-non legume intercropping systems and crop rotations. Hungria and Stacey (1997) reported enhanced growth and yield of intercropped corn and bean as compared to the monocrops and postulated that this increase might be due to the reciprocal stimulation of *A. lipoferum* and *R. tropici* in the soil by the root exudates of corn and bean. To our knowledge this is the first report of LCO enhancement of photosynthesis in legumes and non-legumes. LCOs, besides mediating the early events of nodulation, also act as signals for enhanced photosynthesis in a number of plants and this opens the possibility of harnessing these signal molecules for improving crop production, and ultimately, world food production.

Example 6

Effect of LCOs on the Photosynthetic Rate of Soybean and Corn Grown Under Field Conditions (Year 2000)

*Rhizobium Leguminosarum* (127K105) and *Sinorhizobium meliloti* (RCR 2011) were cultured in modified Bergerson minimal media (Spaink et al., 1992) for four days, when the $OD_{(620)}$ of the culture had reached 0.37 for *S. meliloti* and 0.28 for *R. leguminosarum*, isoflavonoid nariginin was added to *R. leguminosarum* to final concentration of 5 μM and luteolin at 5 μM was added to *S. meliloti*. The cultures were further incubated for five days and they were extracted using the method as described for *Bradyrhizobium japonicum*. LCO of *R. leguminosarum* eluted at 27-31 min of HPLC run while that of *S. melilotieluted* at 35-38 min.

LCO of *R. leguminosarum* enhanced photosynthesis of soybean and was more effective as compared to the LCO of *S. meliloti*. LCO from *S. meliloti* enhanced the photosynthesis of corn (Tables 4 & 5).

TABLE 4

Effect of LCOs of *Rhizobium leguminosarum* (127K105) and *Sinorhizobium meliloti* (RCR 2011) on photosynthetic rates of soybean (cv Bayfield) two days after treatment TABLE 4-continued Effect of LCOs of *Rhizobium leguminosarum* (127K105) and *Sinorhizobium meliloti* (RCR 2011) on photosynthetic rates of soybean (cv Bayfield) two days after treatment

| Treatment | Photo-synthesis (μmol $CO_2$ $m^{-2}$ $s^{-1}$) | Conduc-tance (mol $H_2O$ $m^{-2}$ $s^{-1}$) | Ci (mmol $CO_2$ $mol^{-1}$) | Transpiration (mmol $H_2O$ $m^{-2}$ $s^{-1}$) |
|---|---|---|---|---|
| LCO from *Rhizobium Leguminosarum* (127K105) $10^{-6}$ M | 14.5 a | 0.26 a | 277.0 a | 3.42 ab |
| LCO from *Rhizobium Leguminasarum* (127K105) $10^{-8}$ M | 16.0 a | 0.29 a | 272.6 a | 4.2 a |
| LCO from *Sinorhizobium meliloti* (RCR 2011) $10^{-6}$ M | 12.36 b | 0.15 bc | 241.0 b | 2.89 b |
| LCO from *Sinorhizobium meliloti* (RCR 2011) $10^{-8}$ M | 14.5 a | 0.26 ab | 272.3 a | 2.89 b |
| Control | 12.03 b | 0.13 c | 224.3 b | 2.72 |
| LSD ($p < 0.05$) | 2.12 | 0.10 | 28.9 | 0.96 |

In column numbers followed by same letters are not significantly different ($p < 0.05$) by ANOVA protected LSD test.

TABLE 5

Effect of LCOs of *Rhizobium leguminosarum* (127K105) and *Sinorhizobium meliloti* (RCR 2011) on photosynthetic rates of corn (cv Pioneer 3921) two days after treatment

| Treatment | Photo-synthesis (μmol $CO_2$ $m^{-2}$ $s^{-1}$) | Conduc-tance (mol $H_2O$ $m^{-2}$ $s^{-1}$) | Ci (mmol $CO_2$ $mol^{-1}$) | Transpiration (mmol $H_2O$ $m^{-2}$ $s^{-1}$) |
|---|---|---|---|---|
| LCO from *Rhizobium Leguminasarum* (127K105) $10^{-6}$ M | 25.9 ab | 0.13 b | 63.8 a | 3.3 bc |
| LCO from *Rhizobium Leguminasarum* (127K105) $10^{-8}$ M | 30.5 ab | 0.17 ab | 78.3 ab | 4.1 ab |
| LCO from *Sinorhizobium meliloti* (RCR 2011) $10^{-6}$ M | 26.9 b | 0.14 b | 57.4 ab | 3.4 bc |
| LCO from *Sinorhizobium meliloti* (RCR 2011) $10^{-8}$ M | 35.1 a | 0.21 a | 88.5 ab | 4.9 a |
| Control | 23.1 b | 0.11 | 42.6 b | 2.7 |
| LSD ($p < 0.05$) | 7.9 | 0.07 | 42.9 | 1.3 |

In column numbers followed by same letters are not significantly different ($p < 0.05$) by ANOVA protected LSD test.

Table 6 shows the effect of foliar spray of LCO on yield of soybean during the year 2000. LCO enhanced all the yield components, LCO at $10^{-6}$ M and $10^{-10}$ M showed the maximum effects. LCO $10^{-6}$ M improved the yield by about 60%. The increase in yield was due to the increase in the number of pods/plant. The 100-seed weight was not increased by LCO spray during the 2000 field season.

TABLE 6

Effect of LCO on yield of soybean (2000 cropping season)

| Treatment | Pods/ plant | Pod weight/ plant (g) | Seeds/ plant | 100-seed weight (g) | Seed yield/ plant (g) | Seed yield (t/ha) |
|---|---|---|---|---|---|---|
| LCO $10^{-6}$ M | 46.8 a | 31.4 a | 118.0 a | 17.4 a | 21.0 a | 10.5 a |
| LCO $10^{-8}$ M | 39.1 b | 24.1 b | 96.4 b | 17.8 a | 16.2 b | 8.1 b |
| LCO $10^{-10}$ M | 47.7 a | 29.1 ab | 117.7 a | 18.1 a | 21.8 a | 10.9 a |
| Control | 28.3 c | 18.7 c | 70.4 c | 17.7 a | 13.2 b | 6.6 b |
| LSD | 7.6 | 5.2 | 18.4 | 2.7 | 3.8 | 1.9 |

In columns numbers followed by same letters are not significantly different ($p < 0.05$) by an ANOVA protected LSD test.
Yields are at 0% seed moisture.
Yields were calculated by sampling 10 randomly selected plants per plot, determining the yield per plant and assuming an average stand of 500,000 plants per ha.

Taken together, the results of Tables 4 and 5 show that the photosynthetic rate-promoting effects observed with the *B. japonicum* LCO NodBj-V($C_{18:1}$, MeFeu) during the 1999 experiments are also observable with LCOs obtained from other rhizobia. Thus, addition of the promiscuous rhizobial strain NGR234, known to promote the nodulation of a wide range of legumes or others, are also expected to enhance the photosynthetic rate of plants similarly to the data presented herein.

Data on the effect of foliar spray of LCO on yield of soybean during the year 2000 also shows a yield-increasing effect, similarto that shown in the year 1999. More specifically, in 2000, LCO application enhanced pods/plant and seed yield. Data suggests that (1) LCO at $10^{-6}$M showed the maximum effect; (2) LCO at $10^{-6}$M improved the yield by more than 100%; and (3) the increase in yield was due to the increase in the number of pods/plant.

It is noteworthy that the 1999 and 2000 cropping seasons were very different. As compared to an average cropping season, 1999 was a hot-dry year while 2000 was a cold-wet year.

Taken together with the 1999 results of the effects of LCO application on the photosynthetic rate and on yield, those of 2000 show that the LCO effect thereon is robust over a wide range of environmental conditions.

Also of note, the LCO application in the field experiments in year 2000 were by spraying whole plots, as opposed to individual plants (1999). Thus, the LCO effects described in the present invention are also observable when using large production application methods.

CONCLUSION

The present invention demonstrates that LCO composition can significantly enhance the photosynthetic rate of legumes and non-legumes grown under laboratory conditions (e.g. greenhouse conditions). Furthermore, these greenhouse condition results are validated in the field using soybean, grape, corn and apple. The LCO effect is further shown to be observable with different LCOs, thereby validating the photosynthetic rate-enhancing activity of LCOs in general. In addition, the present invention shows that the photosynthetic rate-enhancing effect of LCOs on plants is robust across the environment field conditions. The similar increases in photosynthetic rates and yield for the tested crop (e.g. soybean) imply that yield increases are to be expected from LCO application on a wide range of crops. The present invention thus provides agricultural compositions and methods by which LCO can be used to enhance the photosynthetic rate, growth and yield of a crop under controlled and diversified field conditions.

Although the present invention has been described herein above by way of preferred embodiments thereof, it can be modified, without departing from the spirit and nature of the subject invention as defined in the appended claims.

REFERENCES

Ayres, P G. 1979, In. Marcelle, R., Clijsters, H., van Poucke, M., Ed. Photosynthesis and Plant Development pp. 343-354. W. Junk, The Hauge, The Netherlands.
Ayres, P G. 1981, Journal of Phytopathology 100:312-318.
Bono et al, 1995, Plant Journal 7:253-260.
Boone et al., 1999. Carbohydrate Research 317:155-163.
Denarie et al., 1993, Cell 74:951-954.
Evans L T., 1975, In L. T. Evans (ed) Crop Physiology. Cambridge University Press, Cambridge, pp 327-355.
Evans L T., 1980, American Scientist 68:388-397.
Fay et al., 1996, New Phytologist 132:425-433.
Fehr et al., 1971, Crop Science 2:929-930.
Fisher et al., 1992, Nature 357:655-660.
Gressent et al., 1999, Proceedings of National Academy of Sciences, USA 96:4704-4709.
Horvath et al., 1993, Plant Journal 4:727-733.
Hungria et al., 1997, Soil Biology and Biochemistry 29:819-830.
Imsande, J., 1989, Journal of Experimental Botany 39:1313-1321.
Imsande, J., 1989, Agronomy Journal 81:549-556.
Inui et al., 1997, Bioscience Biotechnology Biochemistry 61:975-978.
Kondorosi A., 1991, In: Advances in Molecular Genetics of Plant-Microbe interactions. H. Hennecke and D. P. S. Verma, eds. Kluwer Academic Publishers, Dordrecht, Netherlands.
Long S R., 1989, Cell 56:203-214.
Lu et al., 1998, Journal of Experimental Botany 49:453-460.
Makela et al., 1999, Physiologia Plantarum 105:45-50.
Maury et al., 1993, Plant Physiology 101:493-497.
Minami et al., 1996, Molecular Plant-Microbe Interact 9:574-583.
Morison, J., 1998. Journal of Experimental Botany 49:443-452.
Morrison et al., 1999, Agronomy Journal 91:685-689.
Moss et al., 1971, Advances in Agronomy 23:317-336.
Neave et al., 1989, Canadian Journal of Forest Research 19:12-17.

Nonomura et al., 1992, Proceedings of the National Academy of Science USA 89:9794-9798.

Osborne, B A., 1989, Plant, Cell and Environment 12:941-946.

Pichon et al., 1993, In: R. Palacios, J. Mora W E Newton eds. New Horizons in Nitrogen fixation. Kluwer Academic Publishers, Dordrecht, The Netherlands pp. 285-290.

Raschke, K., 1979, In: Haupt, W., Feinleib M. E. eds. Physiology of movements. Vol. 7 Encyclopedia of Plant Physiology. Springer Verlag, Berlin 383441.

SAS Institute Inc. 1989. SAS users guide, Version 6, Cary, USA pp 1673.

Sasaki et al., 1995, Journal of Fermentation and Bioengineering 79:453-457.

Schmidt et al., 1988, Proceedings of National Academy of Sciences, USA 85:8587-8582.

Schulaman et al., 1997, Development 124:4887-4895.

Schultze et al., 1994, Proceedings of National Academy of Sciences, USA 92:2706-2709.

Shabayev et al., 1996, Biology and Fertility of Soils 23:425-430.

Spaink et al., 1991, Nature 354:125-130.

Spaink et al., 1992, Molecular Plant-Microbe Interactions 5:72-80.

Stacey et al., 2000, In: Biology of Plant-Microbe Interactions, Vol 2 p120-125. Ed. P. J. G. M. de Wit, Ton Bisseling and W. J. Stietema.

Staehelin et al., 1994, Proceedings of National Academy of Sciences, USA 91:2196-2200.

Talbott et al., 1996, Plant, Cell and Environment 19:1188-1194.

Thomas et al., 1983, Crop Science 23:453-456.

Truchet et al., 1991, Nature 351:670-673.

Vance et al., 1991, Annual review of Plant Physiology and Plant Molecular Biology 42:373-392.

What is claimed is:

1. A method for enhancing the photosynthetic rate and resulting growth of plants, said method comprising the step of spraying the leaves of the plants with a composition consisting essentially of a lipochitooligosaccharide (LCO) in a concentration of about $10^{-10}$ M to about $10^{-6}$M present in an agriculturally suitable carrier medium; wherein said LCO is obtained from a rhizobia selected from *Bradyrhizobium japonicum, Thizobium meliloti* and *Rhizobium leguminosarum*, and wherein said plant is a legume.

2. The method of claim 1, wherein said plant is a member of the Fabaceae family.

3. The method of claim 2, wherein said plant is selected from the group consisting of soybean, bean, alfalfa and clover.

* * * * *